US011426097B1

United States Patent
Lynn et al.

(10) Patent No.: US 11,426,097 B1
(45) Date of Patent: Aug. 30, 2022

(54) ROTARY VALVE ASSEMBLIES AND METHODS OF USE FOR BREATH SAMPLE CARTRIDGE SYSTEMS

(71) Applicant: Hound Labs, Inc., Oakland, CA (US)

(72) Inventors: Michael Scott Lynn, Piedmont, CA (US); Joseph A. Heanue, Oakland, CA (US); Kevin M. Limtao, Temple City, CA (US); Jeffrey A. Schuster, Alameda, CA (US); Peter A. Holst, Los Altos, CA (US)

(73) Assignee: Hound Labs, Inc., Oakland, CA (US)

( * ) Notice: Subject to any disclaimer, the term of this patent is extended or adjusted under 35 U.S.C. 154(b) by 9 days.

(21) Appl. No.: 16/655,182

(22) Filed: Oct. 16, 2019

Related U.S. Application Data

(60) Provisional application No. 62/821,900, filed on Mar. 21, 2019, provisional application No. 62/746,858, filed on Oct. 17, 2018.

(51) Int. Cl.
*A61B 5/097* (2006.01)
*F16K 1/36* (2006.01)
(Continued)

(52) U.S. Cl.
CPC ............. *A61B 5/097* (2013.01); *F16K 1/36* (2013.01); *F16K 1/42* (2013.01); *F16K 1/46* (2013.01);
(Continued)

(58) Field of Classification Search
CPC . A61B 5/097; A61B 2010/0087; A61B 5/082; F16K 1/44; F16K 1/36; F16K 1/46; F16K 1/42; F16K 1/34; F16K 31/52408
See application file for complete search history.

(56) References Cited

U.S. PATENT DOCUMENTS 3,086,833 A   4/1963 Streak et al.
3,393,108 A * 7/1968 Jones ..................... A61B 5/097
                                                156/253
(Continued)

FOREIGN PATENT DOCUMENTS

EP   0132313 B1   9/1991
EP   2781917 A1   9/2014
(Continued)

OTHER PUBLICATIONS

Adams, I.B. et al., "Cannabis: pharmacology and toxicology in animals and humans," Addiction, Nov. 1996;91 (11):1585-614, PubMed abstract 8972919.
(Continued)

*Primary Examiner* — David Colon-Morales
(74) *Attorney, Agent, or Firm* — Mahamedi IP Law LLP

(57) ABSTRACT

An example breath collection and sampling device disclosed herein comprises a cartridge housing having a breath capture module, and a rotary valve operatively coupling a mouthpiece with the breath capture module. The rotary valve can have an open position where breath of a user can pass through the rotary valve, across capture sites of the breath capture module, and into a vacuum port, and a closed position for sealing the breath capture module from fluid passing through the rotary valve, while allowing the breath capture module to be exposed to a reagent for subsequent analysis of contents within the captured breath.

19 Claims, 11 Drawing Sheets

(51) Int. Cl.
  *F16K 1/42* (2006.01)
  *F16K 1/46* (2006.01)
  *F16K 31/524* (2006.01)
  *A61B 10/00* (2006.01)
(52) U.S. Cl.
  CPC .............. *F16K 31/52408* (2013.01); *A61B 2010/0087* (2013.01)

(56) References Cited

U.S. PATENT DOCUMENTS

| | | | |
|---|---|---|---|
| 3,676,072 | A | 7/1972 | Krivis et al. |
| 4,133,202 | A | 1/1979 | Marple |
| 4,232,667 | A | 11/1980 | Chalon et al. |
| 4,288,344 | A | 9/1981 | Reiss |
| 4,771,005 | A | 9/1988 | Spiro |
| 5,026,027 | A * | 6/1991 | Hamilton ............... A61B 5/097 251/298 |
| 5,103,857 | A * | 4/1992 | Kuhn ................... F16K 21/04 137/315.13 |
| 5,140,993 | A * | 8/1992 | Opekun, Jr ............ A61B 5/097 422/84 |
| 5,361,771 | A | 11/1994 | Craine et al. |
| 5,589,346 | A | 12/1996 | Kanan et al. |
| 5,922,610 | A | 7/1999 | Alving et al. |
| 6,067,983 | A * | 5/2000 | Stenzler ................ A61B 5/097 128/204.23 |
| 6,326,159 | B1 | 12/2001 | Ullman et al. |
| 6,460,539 | B1 | 10/2002 | Japuntich et al. |
| 6,537,823 | B1 | 3/2003 | Smith |
| 6,582,376 | B2 * | 6/2003 | Baghdassarian ..... A61B 5/0836 600/529 |
| 6,605,444 | B1 | 8/2003 | Klein et al. |
| 7,059,349 | B2 * | 6/2006 | Breda ................... E03C 1/023 137/625.11 |
| 7,364,553 | B2 * | 4/2008 | Paz ....................... A61B 5/087 600/529 |
| 7,547,285 | B2 * | 6/2009 | Kline .................... A61B 5/097 600/529 |
| 8,237,118 | B2 | 8/2012 | Prox et al. |
| 8,586,932 | B2 | 11/2013 | Rousso et al. |
| 8,705,029 | B2 | 4/2014 | Palmskog et al. |
| 8,707,758 | B2 | 4/2014 | Keays |
| 8,955,366 | B2 * | 2/2015 | Abraham-Fuchs ......................... G01N 33/497 73/23.3 |
| 9,429,564 | B2 | 8/2016 | Beck |
| 9,617,582 | B2 | 4/2017 | Milton et al. |
| 9,709,581 | B1 * | 7/2017 | Gordon ................. A61B 5/082 |
| 9,709,582 | B1 | 7/2017 | Gordon et al. |
| 9,726,684 | B1 | 8/2017 | Gordon et al. |
| 9,921,234 | B1 | 3/2018 | Lynn et al. |
| 9,933,445 | B1 | 4/2018 | Lynn et al. |
| 9,945,878 | B1 | 4/2018 | Gordon et al. |
| 9,970,950 | B1 | 5/2018 | Lynn et al. |
| 9,976,944 | B2 | 5/2018 | Olin et al. |
| 10,226,201 | B2 * | 3/2019 | Ahmad ................. A61B 5/082 |
| 10,247,742 | B1 | 4/2019 | Lynn et al. |
| 10,408,850 | B1 | 9/2019 | Gordon et al. |
| 10,557,563 | B2 * | 2/2020 | Thurau ................. F16K 31/563 |
| 10,641,783 | B2 | 5/2020 | Lynn et al. |
| 10,955,428 | B2 | 3/2021 | Lynn et al. |
| 11,026,596 | B1 | 6/2021 | Lynn et al. |
| 11,187,711 | B1 | 11/2021 | Lynn et al. |
| 2002/0177232 | A1 | 11/2002 | Melker et al. |
| 2003/0153844 | A1 | 8/2003 | Smith et al. |
| 2004/0043479 | A1 | 3/2004 | Briscoe et al. |
| 2005/0105077 | A1 | 5/2005 | Padmanabhan et al. |
| 2005/0137491 | A1 | 6/2005 | Paz et al. |
| 2006/0094123 | A1 | 5/2006 | Day et al. |
| 2006/0257941 | A1 | 11/2006 | McDevitt et al. |
| 2007/0031283 | A1 | 2/2007 | Davis et al. |
| 2007/0077660 | A1 | 4/2007 | Glas |
| 2008/0004542 | A1 | 1/2008 | Allen et al. |
| 2008/0045825 | A1 | 2/2008 | Melker et al. |
| 2009/0017555 | A1 | 1/2009 | Jehanli et al. |
| 2010/0297635 | A1 | 11/2010 | Olin et al. |
| 2011/0086364 | A1 | 4/2011 | Takkinen et al. |
| 2012/0302907 | A1 | 11/2012 | Palmskog et al. |
| 2013/0006068 | A1 | 1/2013 | Gemer et al. |
| 2013/0021153 | A1 | 1/2013 | Keays |
| 2013/0102018 | A1 | 4/2013 | Schentag et al. |
| 2013/0165806 | A1 | 6/2013 | Wondka et al. |
| 2014/0094391 | A1 | 4/2014 | McDevitt et al. |
| 2014/0276100 | A1 | 9/2014 | Satterfield et al. |
| 2014/0288454 | A1 | 9/2014 | Paz et al. |
| 2014/0366609 | A1 | 12/2014 | Beck et al. |
| 2015/0025407 | A1 * | 1/2015 | Eichler ................. A62B 23/06 600/532 |
| 2015/0033824 | A1 | 2/2015 | Hammarlund et al. |
| 2015/0065901 | A1 * | 3/2015 | Bhatnagar ............. A61B 5/082 600/532 |
| 2015/0265184 | A1 * | 9/2015 | Wondka ............... A61B 5/6819 600/532 |
| 2015/0305651 | A1 | 10/2015 | Attariwala et al. |
| 2015/0369830 | A1 | 12/2015 | Crichlow |
| 2016/0000358 | A1 | 1/2016 | Lundin et al. |
| 2016/0299125 | A1 | 10/2016 | Cristoni et al. |
| 2017/0128692 | A1 | 5/2017 | Christopher et al. |
| 2017/0184609 | A1 | 6/2017 | Milton et al. |
| 2017/0197213 | A1 | 7/2017 | Nielsen et al. |
| 2017/0303822 | A1 | 10/2017 | Allsworth et al. |
| 2017/0303823 | A1 | 10/2017 | Allsworth et al. |
| 2018/0120278 | A1 | 5/2018 | Hoorfar et al. |
| 2018/0224471 | A1 | 8/2018 | Lynn et al. |
| 2018/0238916 | A1 | 8/2018 | Lynn et al. |
| 2018/0243523 | A1 | 8/2018 | Nason et al. |
| 2018/0306775 | A1 | 10/2018 | Beck et al. |
| 2020/0147333 | A1 | 5/2020 | Stoll et al. |
| 2020/0182892 | A1 | 6/2020 | Lynn et al. |
| 2020/0245898 | A1 | 8/2020 | Heanue et al. |
| 2020/0245899 | A1 | 8/2020 | Heanue et al. |
| 2020/0278275 | A1 | 9/2020 | Turgul et al. |
| 2020/0300876 | A1 | 9/2020 | Lynn et al. |
| 2021/0330516 | A1 | 10/2021 | Letourneau et al. |

FOREIGN PATENT DOCUMENTS

| | | |
|---|---|---|
| WO | WO-9014043 A1 | 11/1990 |
| WO | WO-2006083269 A2 | 8/2006 |
| WO | WO-2011029889 A1 | 3/2011 |
| WO | WO-2016065300 A1 | 4/2016 |
| WO | WO-2018185164 A1 | 10/2018 |
| WO | WO-2018211280 A1 | 11/2018 |
| WO | WO-2019011750 A1 | 1/2019 |
| WO | WO-2020097382 A1 | 5/2020 |
| WO | WO-2020159698 A1 | 8/2020 |

OTHER PUBLICATIONS

Al-Asmari, Ahmed et al., "Method for the quantification of diamorphine and its metabolites in pediatric plasma samples by liquid chromatography-tandem mass spectrometry," Journal of Analytical Toxicology, vol. 34, May 2010.

Alexander, Brentan R., "Design of a microbreather for two-phase microchannel devices", Dissertation submitted to Massachusetts Institute of Technology. Dept. of Mechanical Engineering, (Jun. 2008), 59 pages.

Aliberti, S, et al., "Serum and exhaled breath condensate inflammatory cytokines in community-acquired pneumonia: a prospective cohort study", Pneumonia (Nathan), (Jun. 23, 2016), 8:8. doi: 10.1186/s41479-016-0009-7. eCollection 2016.

Andrews, Travis M., "Breathalyzers of the Future Today," The Atlantic, Jun. 2, 20137. Downloaded from the Internet on Feb. 4, 2019, http://www.theatlantic.com/health/archive/2013/06/breathalyzers-of-the-future-today/277249/.

Atkinson, H.C et al., "Drugs in human milk. Clinical pharmacokinetic considerations." Clin Pharmacokinet. Apr. 1988;14(4):217-40, PubMed abstract 3292101.

(56) References Cited

OTHER PUBLICATIONS

Azorlosa, J.L et al., "Marijuana smoking: effect of varying delta 9-tetrahydrocannabinol content and numberof puffs," J. Pharmacol. Exper. Ther 1992;261:114, abstract.
Bailey, J.R et al., "Fetal disposition of delta 9-tetrahydrocannabinol (THC) during late pegnancy in the rhesus monkey," Toxicol Appl Pharmacol. Sep. 15, 1987;90(2):315-21, abstract.
Bajaj, P., and F.T. Ishmael, "Exhaled breath condensates as a source for biomarkers for characterization of inflammatory lung diseases", Journal of Analytical Sciences, Methods and Instrumentation, (Mar. 20, 2013), 3(01):17.
Baker, D. et al., "Cannabinoids control spasticity and tremor in a multiple sclerosis model," Nature, Mar. 2, 2000;404(6773):84-7, abstract.
Balabanova, S. et al., "Detection of drugs in sweat," Belt Gerichtl Med. 1990;48:45-9, abstract.
Bashir, W. et al., "Spectrophotometric Determination of Acetone in Acetic Acid", Microchemical Journal, 1983, 28, pp. 77-81.
Beaudet L, Rodriguez-Suarez R, Venne MH, Caron M, Bédard J, Brechler V, Parent S, Bielefeld-Sévigny M. "AlphaLISA immunoassays: the No. wash alternative to ELISAs for research and drug discovery", Nature Methods, (Dec. 2008), 5(12):an8-9.
Beck, O., et al., "Detection of drugs of abuse in exhaled breath using a device for rapid collection: comparison with plasma, urine and self-re porting in 47 drug users" Journal of breath research, (Apr. 25, 2013), 7(2):026006.
Beck, Olof et al., "Detection of Delta9-tetrahydrocannabinol in exhaled breath collected from cannabis users," Journal of Analytical Toxicology, vol. 35, Oct. 2011.
Benowitz, Neal L. et al., "Metabolic and psychophysiologic studies of cannabidiol-hexobarbital interaction," Clinical Pharmacology and Therapeutics (1980) 28, 115-120, abstract.
Blanc, Jennifer A. et al., "Adsorption losses from urine-based cannabinoid calibrators during routine use," Clin. Chem. 39/8, 1705-1712 (1993).
Bloom, A.S., Effect of delta9-tetrahydrocannabinol on the synthesis of dopamine and norepinephrine in mouse brain synaptosomes, J Pharmocol Exp Ther. Apr. 1982;221(1):97-103.
Bornheim, Lester M. et al., "Characterization of cytochrome P450 3A inactivation by cannabidiol: possible involvement of cannabidiol-hydroxyquinone as a P450 inactivator," Chem. Res. Toxicol., 1998, 11 (10), pp. 1209-0450.
Bornheim, L.M et al., "Human hepatic microsomal metabolism of delta 1-tetrahydrocannabinol," Drug Metab Dispos. Mar.-Apr. 1992;20(2):241-6, PubMed abstract 1352216.
Brenneisen, R et al., "The effect of orally and rectally administered delta 9-tetrahydrocannabinol on spaticity: a pilot study with 2 patients," Int J Clin Pharmocol Ther. Oct. 1996;34(10):446-52.
Brunet, B. et al., "Validation of large white pig as an animal model for the study of cannabinoids metabolism: application to the study of THC distribution in issues," Forensic Sci Int. Sep. 12, 2006;161(2-3):169-74, PubMed abstract 16859848.
Burstein, S. et al., "Isolation and characterization of two major urinary metabolites of 1-tetrahydrocannabinol," Science, Apr. 28, 1972;176(4033):422-3, PubMed abstract 5026162.
Cami, J. et al., "Effect of subject expectancy on the THC intoxication and disposition from smoked hashish cigarettes," Pharmacology Biochemistry and Behavior, vol. 40, Issue 1, Sep. 1991, pp. 115-119.
Carpenter, C.T., Price PV, Christman BW. Exhaled breath condensate isoprostanes are elevated in patients with acute lung injury or ARDS. Chest. Dec. 1, 1998;114(6):1653-9.
Cecinato, A., Balducci C, Perilli M., "Illicit psychotropic substances in the air: The state-of-art", Sci Total Environ, (Jan. 1, 2016), 539:1-6. doi: 10.1016/j.scitotenv.2015.08.051. Epub Sep. 8, 2015. PMID: 26360454.
Challapalli, P.V. et al., "In vitro experiment optimization for measuring tetrahydrocannabinol skin permeation," Int J Pharm. Jul. 25, 2002;241(2):329-39, PubMed abstract 12100860.

Chaturvedi, Arvind K., "Postmortem aviation forensic toxicology: an overview," Journal of Analytical Toxicology, vol. 34, May 2010.
Chiang, C. Nora et al., "Prenatal drug exposure: kinetics and dynamics," NIDA Research Monograph 60, 1985.
Christophersen, Asbjorg Solberg et al., "Tetrahydrocannabinol stability in whole blood: plastic versus glass containers," Journal of Analytical Toxicology, vol. 10, July/Aug. 1986.
Chuah K, Wu Y, Vivekchand SR, Gaus K, Reece PJ, Micolich AP, Gooding JJ. "Nanopore blockade sensors for ultrasensitive detection of proteins in complex biological samples", Nature communications, (May 8, 2019), 10(1):1-9. (9 pages).
Cirimele, V. et al., "Testing human hair for cannabis. III. Rapid screening procedure for the simultaneous identification of delta9-tetrahydrocannabinol, cannabinol, and cannabidiol," Journal of Analytical Toxicology, vol. 20, Jan./Feb. 1996.
Cone, Edward J. et al., "In vivo adulteration: excess fluid ingestion causes false-negative marijuana and cocaine urine test results," Journal of Analytical Toxicology, vol. 22, Oct. 1998.
Cone, Edward J. et al., "Marijuana-laced brownies: behavioral effects, physiologic effects, and urinalysis in humans following ingestion," Journal of Analytical Toxicology, vol. 12, Jul./Aug. 1988.
Cone, EJ, Johnson RE, Darwin WD, Yousefnejad D, Mell LD, Paul BD, Mitchell J., "Passive inhalation of marijuana smoke: urinalysis and room air levels of delta-9-tetrahydrocannabinol", J Anal Toxicol. (May-Jun 1987), 11 (3):89-96. doi: 10.1093/jat/11.3.89. PMID: 3037193.
Crouch, Dennis J. et al., "An evaluation of selected oral fluid point-of-collection drug-testing devices," Journal of Analytical Toxicology, vol. 29, May/Jun. 2005.
Crouch, D.J., "Oral fluid collection: the neglected variable in oral fluid testing," Forensic Sci Int. Jun. 10, 2005;150(2-3):165-73, PubMed abstract 15899565.
D'Ambrosio, M. et al., "Point-of-care quantification of blood-borne filarial parasites with a mobile phone microscope", Science Translational Medicine (May 6, 2015), vol. 7, Issue 286, p. 286re4. 10 pages.
Day, David et al., "Detection of THCA in oral fluid by GC-MS-MS," Journal of Analytical Toxicology, vol. 30, Nov./Dec. 2006.
Doran, GS, Deans R, De Filippis C, Kostakis C, Howitt JA., "Work place drug testing of police officers after THC exposure during large vol. cannabis seizures", Forensic Sci Int. (Jun. 2017), 275:224-233. doi: 10.1016/j.forsciint.2017.03.023. Epub 2017 Apr. 2. PMID: 28412574.
D'Sourza, Deepak Cyril et al., "The psychotomimetic effects of intravenous delta-9-tetrahydrocannabinol in healthy individuals: implications for psychosis," Neuropsychopharmacology (2004) 29, 1558-1572.
"Drug detection, health monitoring etc.", SensAbues AB—Innovation, downloaded on Mar. 25, 2019 from http://sensabues.com/innovation.
Dunk, et al., "Development of a Portable Marijuana Breathalyzer", (Mar. 2018), URL=http://https://houndlabs.com/wp-content/uploads/2018/03/Hound-TRT-Pittcon-Poster.pdf.
Ellis, George M. Jr. et al. "Excretion patterns of cannabinoid metabilites after last use," 420 Magazine, Oct. 4, 2011, downloaded from https://www.420magazine.com/forums/drug-testing-urine/153724.
Ellis, G.M. Jr. et al., "Excretion patterns of cannabiniod metabolites after last use in a group of chronic users," Clin Pharmacol Ther. Nov. 1985;38(5):572-8, PubMed abstract 3902318.
ElSohly, M. et al., "Potency trends of Delta9-THC and other cannabinoids in confiscated marijuana from 1980-1997," Journal of Forensic Sciences, vol. 45, No. 1, 2000, pp. 24-30.
Emelyanov, A., et al., "Elevated concentrations of exhaled hydrogen peroxide in asthmatic patients", Chest, (Oct. 1, 2001), 120(4):1136-9.
"SensAbues AB—Next generation drug detection and health monitoring", SensAbues AB—Home, downloaded on Mar. 25, 2019 from http://sensabues.com/home.
"Exhaled breath biological sample matrix. EB", SensAbues AB—Product, downloaded on Mar. 25, 2019 from http://sensabues.com/product.

(56) References Cited

OTHER PUBLICATIONS

"Exhaled breath sampling company", SensAbues AB—About, downloaded on Mar. 25, 2019 from http://sensabues.com/about.
"FAIMS Breathalyzer Device", downloaded on Mar. 25, 2019 from https://algernonpharmaceuticals.com/faims-breathalyzer-device/.
Feng, Shixia et al., "Simultaneous analysis of Delta9-THC and its major metabolites in urine, plasma, and meconium by GC-MS using an immunoaffinity extraction procedure," Journal of Analytical Toxicology, vol. 24, Sep. 2000.
Fraser, A.D. et al., "Monitoring urinary excretion of cannabinoids by fluorescence-polarization immunoassay: a cannabiniod-to-creatinine ratio study," Ther Drug Monit. Dec. 2002;24(6):746-50, PubMed abstract 12451292.
Fraser, A.D. et al., "Urinary excretion profiles of 11-nor9-carboxy-delta9-tetrahydrocannabinol and 11-hydroxy-delta9-THC: cannabinoid metabolites to creatinine ratio study IV," Forensic Sci Int. Jul. 16, 2004;143(2-3):147-52, PubMed abstract 15240035.
Fraser, A.D. et al., "Urinary excretion profiles of 11-nor-9-carboxy-Delta9-tetrahydrocannabinol. Study III. A Delta9-THC-COOH to creatinine ratio study," Forensic Sci Int. Nov. 26, 2003;137(2-3):196-202, PubMed abstract 14609657.
Garrett, Edward R. et al., "Physicochemical properties, solubility, and protein binding of Delta9-tetrahydrocannabinol," J Pharm Sci. Jul. 1974;63(7):1056-64, abstract.
Garrett, E.R. et al., "Pharmacokinetics of delta9-tetrahydrocannabinol in dogs," J Pharm Sci. Mar. 1977;66(3):395-407, PubMed abstract 845807.
Gjerde, H. et al., "Incidence of alcohol and drugs in fatally injured car drivers in Norway," Accid Anal Prev. Aug. 1993;25(4):479-83, PubMed abstract 8357462.
Gjerde, Hallvard et al., "Comparison of drug concentrations in blood and oral fluid collected with the Intercept® sampling device," Journal of Analytical Toxicology, vol. 34, May 2010.
Goodwin, R.S. et al., "Delta(9)-tetrahydrocannabinol, 11-hydroxy-delta(9)-tetrahydrocannabinol and 11-nor-9-carboxy-delta(9)-tetrahydrocannabinol in human plasma after controlled oral administration of cannabinoids," Ther Drug Monit. Aug. 2006;28(4):545-51, PubMed abstract 16885723.
Gramse G, Dols-Pérez A, Edwards MA, Fumagalli L, Gomila G. Nanoscale measurement of the dielectric constant of supported lipid bilayers in aqueous solutions with electrostatic force microscopy. Biophysical journal. Mar. 19, 2013;104(6):1257-62.
Green, Mitchell D et al., "Glucuronidation of opioids, carboxylic acid-containing drugs, and hydroxylated xenobiotics catalyzed by expressed monkey UDP-glucuronosyltransferase 2B9 protein," Drug Metabolism and Disposition, vol. 25, No. 12, (1997).
Grob NM, Aytekin M, Dweik RA. "Biomarkers in exhaled breath condensate: a review of collection, processing and analysis", Journal of breath research, (Sep. 8, 2008), 2(3):037004.
Gross, Stanley J. et al., "Detection of recent cannabis use by saliva Delta9-THC radioimmunoassay," Journal of Analytical Toxicology, vol. 9, Jan./Feb. 1985.
Grotenhermen, F., "Pharmacokinetics and pharmacodynamics of cannabinids," Clin Pharmacokinet. 2003;42(4):327-60, PubMed abstract 12648025.
Gustafson, R.A et al., "Validated method for the simultaneous determination of Delta 9-tetrahydrocannabinol (THC), 11-hydroxy-THC and 11-nor-9-carboxy-THC in human plasma using solid phase extraction and gas chromatography-mass spectrometry with positive chemical ionization," J. Chromatogr B Analyt Technol Biomed Life Sci, Dec. 5, 2003;798(1):145-54, PubMed abstract 14630369.
Gustafson, Richard A. et al., "Urinary cannabinoid detection times after controlled oral administration of Delta9-tetrahydrocannabinol to humans," Clinical Chemistry 49:7, 1114-1124 (2003).
Gustafson, Richard A. et al., "Urinary pharmacokinetics of 11-Nor-9-carboxy-delta9-tetrahydrocannabinol after controlled oral delat9-tetrahydrocannabinol administration," Journal of Analytical Toxicology, vol. 28, Apr. 2004.

Guy, G.W. et al., "A phase I, double blind, three-way crossover study to assess the pharmacokinetic profile of cannabis based medicine extract (CBME) administered sublingually in variant cannabinoid ratios in normal healthy male volunteers (GWPK0215)," Journal of Cannabis Therapeutics, vol. 3, No. 4, 2003, pp. 121-152.
Hall, B.J. et al., "Determination of cannabinoids in water and human saliva by solid-phase microextraction and quadrupole ion trap gas chromatography/mass spectrometry," Anal chem. May 1, 1998;70(9):1788-96, PubMed abstract 9599579.
Halldin, M.M. et al., "Identification of in vitro metabolites of delta 1-tetrahydrocannabinol formed by human livers," Drug Metab Dispos. Jul.-Aug. 1982;10(4):297-301, PubMed abstract 6126323.
Hampson, A.J. et al., "Cannabidiol and (−)delta9-tetrahydrocannabinol are neuroprotective antioxidants," Proc Natl Acad Sci U.S.A. Jul. 7, 1998; 95(14): 8268-8273.
Hanson, V.W. et al., "Comparison of 3H- and 125I-radioimmunoassay and gas chromatography/mass spectrometry for the determination of delta9-tetrahydrocannabinol and cannabinoids in blood and serum," Journal of Analytical Toxicology, vol. 7, Mar./Apr. 1983.
Harder, S. et al., "Concentration-effect relationship of delta-9-tetrahydrocannabiol and prediction of psychotropic effects after smoking marijuana," Int J Clin Pharmacol Ther. Apr. 1997;35(4):155-9, PubMed abstract 9112136.
Harvey, D.J. et al., "Metabolites of cannabidiol identified in human urine," Xenobiotic, Mar. 1990;20(3):303-20, PubMed abstract 2336840.
Hasan, R.A., et al., "Lipoxin A4 and 8-isoprostane in the exhaled breath condensate of children hospitalized for status asthmaticus", Pediatric critical care medicine: a journal of the Society of Critical Care Medicine and the World Federation of Pediatric Intensive and Critical Care Societies, (Mar. 2012), 13(2):141.
Hawks, Richard L., "The Analysis of Cannabinoids in Biological Fluids," NIDA Research Monograph 42, 1982.
Hazekamp, Arno et al., "Cannabis; extracting the medicine," thesis/dissertation 2007.
Heishman, Stephen J. et al., "Effects of tetrahydrocannabinol content on marijuana smoking behavior, subjective reports, and performance," Pharmacology Biochemistry and Behavior, vol. 34, Issue 1, Sep. 1989, pp. 173-179, abstract.
Himes, Sarah K. et al., "Cannabinoids in exhaled breath following controlled administration of smoked cannabis," Clinical chemistry 59:12 1780-1789 (2013).
Huang, Wei et al., "Simultaneous determination of delta9-tetrahydrocannabinol and 11-nor-9-carboxy-delta9-tetrahydrocannabinol in human plasma by solid-phase extraction and gas chromatography-negative ion chemical ionization-mass spectrometry," Journal of Analytical Toxicology, vol. 25, Oct. 2001.
Huestis, M.A. et al., "Characterization of the absorption phase of marijuana smoking," Clin Pharmacol Ther. Jul. 1992;52(1):31-41, PubMed abstract 1320536.
Huestis, Marilyn A. et al., "Alternative testing matrices," chapter 11 of the Drug Abuse Handbook, 1998 CRC Press LLLC, ISBN 0-8493-2637-0.
Huestis, Marilyn A. et al., "Blood cannabinoids. I. Absorption of THC and formation of 11-OH-THC and THCCOOH during and after smoking marijuana," Journal of Analytical Toxicology, vol. 16, Sep./Oct. 1992.
Huestis, Marilyn A. et al., "Blood cannabinoids. II. Models for the prediction of time of marijuana exposure from plasma concentraitons of delta9-tetrahydrocannabinol (THC) and 11-nor-9-carboxy-delta9-tetrahydrocannabinol (THCCOOH)," Journal of Analytical Toxicology, vol. 16, Sep./Oct. 1992.
Huestis, Marilyn A. et al., "Cannabinoid concentrations in hair from documented cannabis users," ForensicSci Int. Jul. 4, 2007; 169(2-3): 129-136.
Huestis, Marilyn A. et al., "Detection times of marijuana metabolites in urine by immunoassay and GC-MS," Journal of Analytical Toxicology, vol. 19, Oct. 1995.
Huestis, Marilyn A. et al., "Differentiating new marijuana use from residual drug excretion in occasional marijuana users," Journal of Analytical Toxicology, vol. 22, Oct. 1998.

(56) References Cited

OTHER PUBLICATIONS

Huestis, Marilyn A. et al., "Estimating the time of last cannabis use from plasma delta9-tetrahydrocannabinol and 11-nor-9-carboxy-delta9-tetrahydrocannabinol concentrations," Clinical Chemistry 51:12 2289-2295 (2005).

Huestis, Marilyn A. et al., "Relationship of delta9-tetrahydrocannabinol concentrations in oral fluid and plasma after controlled administration of smoked cannabis," Journal of Analytical Toxicology, vol. 28, Sep. 2004.

Huestis, Marilyn A. et al., "Urinary excretion profiles of 11-nor-9-carboxy-delta9-tetrahydrocannabinol in humans after single smoked doses of marijuana," Journal of Analytical Toxicology, vol. 20, Oct. 1996.

Huestis, Marilyn A., "Human cannabinoid pharmacokinetics," Chem Biodivers. Aug. 2007; 4(8): 1770-1804.

Hunt, C.A. et al., "Evidence that cannabidiol does not significantly alter the pharmacokinetics of tetrahydrocannabinol in man," J Pharmacokinet Biopharm. Jun. 1981;9(3):245-60, PubMed abstract 6270295.

Hunt, C.A. et al., "Tolerance and disposition of tetrahydrocannabinol in man," J Pharmacol Exp Ther. Oct. 1980;215(1):35-44, PubMed abstract 6256518.

"Information for health care professionals: cannabis (marihuana, marijuana) and the cannabinoids," Health Canada, Feb. 2013.

International Preliminary Report on Patentability dated Jul. 27, 2021, for International Patent Application No. PCT/US2020/13553, 8 pages.

International Preliminary Report on Patentability dated May 11, 2021, for International Patent Application No. PCT/US2019/060342, 9 pages.

International Search Report dated Apr. 6, 2020, for International Patent Application No. PCT/US2020/13553, 2 pages.

International Search Report dated Jan. 23, 2020, for International Patent Application No. PCT/US2019/060342, 2 pages.

Iribarne, C. et al., "Involvement of cytochrome P450 3A4 enzyme in the N-demethylation of methadone in human liver microsomes," Chem Res Toxicol. Mar. 1996;9(2):365-73, PubMed abstract 8839037.

Jehanli, A. et al., "Blind trials of an onsite saliva drug test for marijuana and opiates," J Forensic Sci. Sep. 2001;46(5):1214-20, PubMed 11569567.

Joern, William A., "Surface adsorption of the urinary marijuana carboxy metabolite: the problem and a partial solution," Letter to the Editor, Journal of Analytical Toxicology, vol. 16, Nov./Dec. 1992.

Johannson, E. et al., "Terminal elimination plasma half-life of delta 1-tetrahydrocannabinol (delta 1-THC) in heavy users of marijuana," Eur J Clin Pharmacol. 1989;37(3):273-7, PubMed abstract 2558889.

Johansson, E. et al., "Determination of delta 1-tetrahydrocannabinol in human fat biopsies from marihuana users by gas chromatography-mass spectrometry," Biomed Chromatogr. Jan. 1989;3(1):35-8, PubMed abstract 2539872.

Johansson, E. et al., "Prolonged apparent half-life of delta 1-tetrahydrocannabinol in plasma of chronic marijuana users," J Pharm Pharmacol. May 1988;40(5):374-5, PubMed abstract 2899638.

Johansson, Eva et al., "Urinary excretion half-life of delta1-tetrahydrocannabinol-7-oic acid in heavy marijuana users after smoking," Journal of Analytical Toxicology, vol. 13, Jul./Aug. 1989.

Jokerst JV, Chen Z, Xu L, NoIley R, Chang E, Mitchell B, Brooks JD, Gambhir SS. A magnetic bead-based sensor for the quantification of multiple prostate cancer biomarkers. PloS One. (Sep. 30, 2015), 10(9):e0139484. (15 pages).

Kadehijian, Leo, "Syva has been a leading developer and manufacturer of drugs-of-abuse tests for more than 30 years," Cannabinoid Issues: Passive inhalation, excretion patterns, and retention times, test result interpretation, Siemens Healthcare Diagnostics Inc., 2009.

Karst, Matthias et al., "Analgesic effect of the synthetic cannabinoid CT-3 on chronic neuropathic pain," JAMA. 2003;290(13):1757-1762.

Kelly, Peggy et al., "Metabolism of tetrahydrocannabinol in frequent and infrequent marijuana users," Journal of Analytical Toxicology, vol. 16, Jul./Aug. 1992.

Kemp, Philip M et al., "Cannabinoids in Humans. I. Analysis of delta9-tetrahydrocannabinol and six metabolites in plasma and urine using GC-MS," Journal of Analytical Toxicology, vol. 19, Sep. 1995.

Kemp, Philip M. et al., "Cannabinoids in Humans. II. The influence of three methods of hydrolysis on the concentration of THC and two metabolites in urine," Journal of Analytical Toxicology, vol. 19, Sep. 1995.

Kidwell, David A. et al., "Testing fordrugs of abuse in saliva and sweat," Journal of Chromatography B: Biomedical Sciences and Applications, vol. 713, Issue 1, Aug. 21, 1998, pp. 111-135, abstract.

Kintz, P. et al., "Testing human hair for cannabis. II. Identification of TCD-COOH by GC-MS-NCI as a unique proof," J Forensic Sci. Jul. 1995;40(4):619-22, PubMed abstract 7595299.

Kintz, Pascal et al., "Detection of cannabis in oral fluid (saliva) and forehead wipes (sweat) from impaired drivers," Journal of Analytical Toxicology, vol. 24, Oct. 2000.

Kintz, Pascal et al., "Sweat testing for heroin and metabolites in a heroin maintenance program, " Clinical Chemistry 43:5, 736-739 (1997).

Klejnowski, K et al. "No. Size Distribution of Ambient Particles in a Typical Urban Site: The First Polish Assessment Based on Long-Term (9 Months) Measurements", The Scientific World Journal, (Oct. 2013), 2013(1):539568.

Kodavanti, U.P. "Respiratory toxicity biomarkers", In Biomarkers in Toxicology, (Jan. 1, 2014) (pp. 217-239). Academic Press.

Kovatsi, Leda et al., "Development and validation of a high-performance liquid chromatography method for the evaluation of niflumic acid cross-reactivity of two commercial immunoassays for cannabinoids in urine," Journal of Analytical Toxicology, vol. 34, May 2010.

Krenke, K. et al., "Inflammatory cytokines in exhaled breath condensate in children with inflammatory bowel diseases", Pediatric pulmonology, (Dec. 2014), 49(12):1190-5.

Kreuz, D.S. et al., "Delta-9-tetrahydrocannabinol: localization in body fat," Science, Jan. 26, 1973;179(4071):391-3, PubMed abstract 4682965.

Krishna, D.R. et al., "Extrahepatic metabolism of drugs in humans," Clin Pharmacokinet. Feb. 1994;26(2):144-60, PubMed abstract 8162658.

Lafolie, P. et al., "Importance of creatinine analyses of urine when screening for abused drugs," Clin. Chem. 37/11, 1927-1931 (1991).

Laloup, M. et al., "Correlation of delta9-tetrahydrocannabinol concentrations determined by LC-MS-MS in oral fluid and plasma from impaired drivers and evaluation of the on-site Drager Drug Test," ForensicSci Int. 2006 Srp 12;161(2-3):175-9, PubMed abstract 16842950.

Law, B. et al., "Forensic aspects of the metabolism and excretion of cannabinoids following oral ingestion of cannabis resin," J Pharm Pharmacol. May 1984;36(5):289-94, PubMed abstract 6145762.

Le Ru EC, Blackie E, Meyer M, Etchegoin PG. Surface enhanced Raman scattering enhancement factors: a comprehensive study. The Journal of Physical Chemistry C. Sep. 20, 2007;111(37):13794-803.

Lee, Sooyeun et al., "Estimation of the measurement uncertainty by the bottom-up approach for the determination of methamphetamine and amphetamine in urine," Journal of Analytical Toxicology, vol. 34, May 2010.

Lemberger, L. et al., "11-hydroxy-9-tetrahydrocannabinol: pharmacology, disposition, and metabolism of a major metabolite of marihuana in man," Science. Jul. 7, 1972;177(4043):62-4, PubMed abstract 5041775.

Lemberger, L. et al., "Delta-9-tetrahydrocannabinol: metabolism and disposition in long-term marihuana smokers," Science. Jul. 2, 1971;173(3991):72-4, PubMed abstract 5087483.

Lemberger, L. et al., "Marihuana: studies on the disposition and metabolism of delta-9-tetrahydrocannabinol in man," Science. Dec. 18, 1970;170(3964):1320-2, PubMed abstract 5479011.

(56) References Cited

OTHER PUBLICATIONS

Lindgren, J.E. et al., "Clinical effects and plasma levels of delta 9-tetrahydrocannabinol (delta 9-THC) in heavy and light users of cannabis," Psychopharmacology (Berl). 1981;74(3):208-12, PubMed 6267648.
"Low cost, non-invasive and non-intrusi", SensAbues AB—Benefits, downloaded on Mar. 25, 2019 from http://sensabues.com/benefits.
Malfait, A.M. "The non psychoactive cannabis constituent cannabidiol is an oral anti-arthritic therapeutic in murine collagen-induced arthritis," Proc Natl Acad Sci USA Aug. 15, 2000;97(17):9561-9566.
Manno, Joseph E et al., "Temporal indication of marijuana use can be estimated from plasma and urine concentrations of delta9-tetrahydrocannabinol, 11-hydroxy-delta9-tetrahydrocannabinol, and 11-nor-delta9-tetrahydrocannabinol-9-carboxylic acid," Journal of Analytical Toxicology, vol. 25, Oct. 2001.
Manolis, Antony et al., "The detection of delta9-tetrahydrocannabinol in the breath of human subjects," Clinical Biochem. 16,229 (1983).
"Marihuana '84," Proceedings of the Oxford Symposium on Cannabis, D.J. Harvy, editor, IRL Press, Oxford 1984.
Martin, B.R. et al., "3H-delta9-tetrahydrocannabinol distribution in pregnant dogs and their fetuses," Res Commun Chem Pathol Pharmacol. Jul. 1977;17(3):457-70, PubMed abstract 897339.
Mason, A.P. et al., "Cannabis: pharmacology and interpretation of effects," J Forensic Sci. Jul. 1985;30(3):615-31, PubMed abstract 2993473.
Mason, A.P. et al., "Ethanol, marijuana, and other drug use in 600 drivers killed in single-vehicle crashes in North Carolina, 1978-1981," J Forensic Sci. Oct. 1984;29(4):987-1026, PubMed abstract 6502125.
Matsunaga, T. et al., "Metabolism of delta 9-tetrahydrocannabinol by cytochrome P450 isozymes purified from hepatic microsomes of monkeys," Life Sci. 1995;56(23-24):2089-95, PubMed abstract 7776836.
Mattes, R.D. et al., "Bypassing the first-pass effect for the therapeutic use of cannabinoids," Pharmacol Biochem Behav. Mar. 1993;44(3):745-7, PubMed abstract 8383856.
Mattes, R.D. et al., "Cannabinoids and appetite stimulation," Pharmacol Biochem Behav. Sep. 1994;49(1):187-95, PubMed abstract 7816872.
Mcburney, L.J. et al., "GC/MS and EMIT analyses for delta9-tetrahydrocannabinol metabolites in plasma and urine of human subjects," Journal of Analytical Toxicology, vol. 10, Mar./Apr. 1986.
Mechoulam, Raphael et al., "Cannabidiol: an overview of some chemical and pharmacological aspects. Part I: chemical aspects," Chemistry and Physics of Lipids 121 (2002) 35-43.
Mechoulam, Raphael, "Plant cannabinoids: a neglected pharmacological treasure trove," Br J Pharmacol. Dec. 2005; 146(7): 913-915.
Meier, H. et al., "Cannabis poisoning after eating salad," Schweiz Med Wochenschr. Feb. 8, 1997;127(6):214-8, PubMed abstract 9157527.
Menkes, D.B. et al., "Salivary THC following cannabis smoking correlates with subjective intoxication and heart rate," Psychopharmacology (Berl). 1991;103(2):277-9, PubMed abstract 1851311.
Mikuriya, Tod H., "Cannabis as a substitute for alcohol: a harm-reduction approach," Journal of Cannabis Therapeutics, vol. 4(1) 2004.
Milman, Garry et al., "Simultaneous quantification of cannabinoids and metabolites in oral fluid by two-dimensional gas chromatography mass spectrometry," J Chromatogr A. Feb. 26, 2010; 1217(9): 1513-1521.
Moeller, M.R et al., "Simultaneous quantitation of delta-9-tetrahydrocannabinol (THC) and 11-nor-9-carboxy-delta-9-tetrahydrocannabinol (THC-COOH) in serum by GC/MS using deuterated internal standards and its application to a smoking study and forensic cases," J Forensic Sci. Jul. 1992;37(4):969-83, PubMed abstract 1324293.

Moldoveanu, Serban C. et al., "Differences in the chemical composition of the particulate phase of inhaled and exhaled cigarette mainstream smoke," Contributions to Tobacco Research 22(4), 290 (2007).
Moore, Christine et al., "Analytical procedure for the determination of the marijuana metabolite 11-nor-delta9-tetrahydrocannabinol-9-carboxylic acid in oral fluid specimens," Journal of Analytical Toxicology, vol. 30, Sep. 2006.
Moore, Christine et al., "Application of two-dimensional gas chromatography with electron capture chemical ionization mass spectrometry to the detection of 11-nor-delta9-tetrahydrocannabinol-9-carboxylic acid (THC-COOH) in hair," Journal of Analytical Toxicology, vol. 30, Apr. 2006.
Moore, Christine et al., "Detection of the marijuana metabolite 11-nor-delta9-tetrahydrocannabinol-9-carboxylic acid in oral fluid specimens and its contribution to positive results in screening assays," Journal of Analytical Toxicology, vol. 30, Sep. 2006.
Moore, Christine et al., "The determination of 11-nor-delta9-tetrahydrocannabinol-9-carboxylic acid (THC-COOH) in hair using negative ion gas chromatography-mass spectrometry and high-vol. injection," Journal of Analytical Toxicology, vol. 25, Oct. 2001.
Morland, J. et al., "Cannabinoids in blood and urine after passive inhalation of cannabis smoke," J Forensic Sci. 1985 Oct;30(4):997-1002, PubMed abstract 2999292.
Mule, S.J. et al., "Active and realistic passive marijuana exposure tested by three immunoassays and GC/MS in urine," Journal of Analytical Toxicology, vol. 12, May/Jun. 1988.
Mura, P. et al., "Evaluation of six rapid tests for screening of cannabis in sweat, saliva and tears," Acta Clin Belg. 1999;53 Suppl 1:35-8, PubMed abstract 10216980.
Mura, P. et al., "THC can be detected in brain while absent in blood," Letter to the Editor, Journal of Analytical Toxicology, vol. 29, Nov./Dec. 2005.
Nadulski T. et al., "Simultaneous and sensitive analysis of Thc, 11-OH-THC, Thc-COOH, CBD, and CBN by GC-MS in plasma after oral application of small doses of THC and cannabis extract," Journal of Analytical Toxicology, vol. 29, Nov./Dec. 2005.
Nadulski T. et al., "Randomized, double-blind, placebo-controlled study about the effects of cannabidiol (CBD) on the pharmacokinetics of Delat9-tetrahydrocannabinol (THC) after oral application of THC verses standardized cannabis extract," Ther Drug Monit. Dec. 2005;27(6):799-810.
Nahas, Gabriel G. et al., "Pharmacokinetics of THC in brain and testis, male gametotoxicity and premature apoptosis of spermatozoa," Human Psycopharmacology: Clinical and Experimental, vol. 17, Issue 2, pp. 103-113, Mar. 2002, abstract.
Niedbala, R. Sam et al., "Detection of marijuana use by oral fluid and urine analysis following single-dose administration of smoked and oral marijuana," Journal of Analytical Toxicology, vol. 25, Jul./Aug. 2001.
Niedbala, R. Sam et al., "Passive cannabis smoke exposure and oral fluid testing. II. Two studies of extreme cannabis smoke exposure in a motor vehicle," Journal of Analytical Toxicology, vol. 29, Oct. 2005.
"N.S. woman who tested positive for pot when she wasn't high to challenge roadside testing laws," CBC Radio, posted Apr. 3, 2019. 6 pages.
Oguma, T., et al., "Clinical contributions of exhaled volatile organic compounds in the diagnosis of lung cancer", PloS one, (Apr. 6, 2017), 12(4):e0174802.
Ohlsson, A. et al., "Plasma delta-9 tetrahydrocannabinol concentrations and clinical effects after oral and intravenous administration and smoking," Clin Pharmacol Ther. Sep. 1980;28(3):409-16, PubMed abstract 6250760.
Ohlsson, Agneta et al., "Single dose kinetics of deuterium labelled delta1-tetrahydrocnnabinol in heavy and light cannabis users," Biological Mass Spectrometry, vol. 9, Issue 1, pp. 6-10, Jan. 1982, abstract.
Olmon RL, Slovick B, Johnson TW, Shelton D, Oh SH, Boreman GD, Raschke MB. Optical dielectric function of gold. Physical Review B. Dec. 2, 20128;86(23):235147.

(56) References Cited

OTHER PUBLICATIONS

Owens, S. Michael et al., I Radioimmunoassay of delta-9-tetrahydrocannabinol in blood and plasma with a solid-phase second-antibody separation method, Clin. Chem. 27/4, 619-624 (1981).
"Owlstone—About", downloaded on Mar. 25, 2019 from https://www.owlstonemedical.com/about/.
"Owlstone—EVOC Probes", downloaded on Mar. 25, 2019 from https://www.owlstonemedical.com/science-technology/evoc-probes/.
"Owlstone—FAIMS technology", downloaded on Mar. 25, 2019 from https://www.owlstonemedical.com/science-technology/faims-technology/.
"Owlstone—Research case studies", downloaded on Mar. 25, 2019 from https://www.owlstonemedical.com/science-technology/research-case-studies/.
"Owlstone Medical—Active Clinical Pipeline", downloaded on Mar. 25, 2019 from https://www.owlstonemedical.com/clinical-pipeline/.
"Owlstone Medical—Products", downloaded on Mar. 21, 2019 from https://www.owlstonemedical.com/products/.
"Owlstone Medical—The Home of Breath Biopsy: A Breathalyzer for Disease", downloaded on Mar. 25, 2019 from https://www.owlstonemedical.com/#.
"Owlstone Medical —The Home of Breath Biopsy: Breath Biopsy—VOC Biomarkers", downloaded on Mar. 25, 2019 from https://www.owlstonemedical.com/#.
Pardon, G, et al., "Aerosol sampling using an electrostatic precipitator integrated with a microfluidic interface", Sensors and Actuators B: Chemical. Feb. 2015, vol. 212, pp. 344-352.
Peel, H.W et al., "Detection of drugs in saliva of impaired drivers," J Forensic Sci. Jan. 1984;29(1):185-9, PubMed abstract 6366113.
Perez-Reyes, M. et al., "Comparison of effects of marihuana cigarettes to three different potencies," Clin Pharmacol Ther. May 1982;31(5):617-24, PubMed abstract 6280918.
Perez-Reyes, M. et al., "Intravenous injection in man of 9-tetrahydrocannabinol and 11-OH-9-tetrahydrocannabinol," Science. Aug. 1, 19728;177(4049):633-5, PubMed abstract 4558903.
Perez-Reyes, M. et al., "The clinical pharmacology and dynamics of marihuana cigarette smoking," J Clin Pharmacol. Aug.-Sep. 1981;21(8-9 Suppl):201S-207S, PubMed abstract 6271825.
Perez-Reyes, Mario, "Marijuana smoking: factors that influence the bioavailability of tetrahydrocannabinol," NIDA Monograph 1990;99:42.
PerkinElmer Inc., "TSA Signal Amplification (TSA) Systems," Document No. 007703_01, 16 pages, accessed at perkinelmer.com/lab-solutions/resources/docs/BRO_tsasignalamplification systems.pdf.
"Pexa—About PExA", downloaded on Mar. 25, 2019 from http://pexa.se/en/about-pexa/.
"Pexa—Analysis", downloaded on Mar. 25, 2019 from http://pexa.se/en/product-services/analysis/.
"Pexa—Business Concept & Vision", downloaded on Mar. 25, 2019 from http://pexa.se/en/about-pexa/business-concept-vision/.
"Pexa—History", downloaded on Mar. 25, 2019 from http://pexa.se/en/about-pexa/history/.
"Pexa—How PExA works", downloaded on Mar. 25, 2019 from http://pexa.se/en/product-services/how-pexa-works/.
"Pexa—Particles in Exhaled Air", downloaded on Mar. 25, 2019 from http://pexa.se/en/.
"Pexa—PExA 2.0", downloaded on Mar. 25, 2019 from http://pexa.se/en/product-services/pexa-2-0/.
"Pexa—Product & Services", downloaded on Mar. 25, 2019 from http://pexa.se/en/product-services/.
"Pexa—Product-Sheet", Sep. 2016.
"Pexa—R&D and publications", downloaded on Mar. 25, 2019 from http://pexa.se/en/product-services/research-development/.
"Pexa—Research areas", downloaded on Mar. 25, 2019 from http://pexa.se/en/respiratory-research/research-areas/.
"Pexa—Respiratory Research Needs", downloaded on Mar. 25, 2019 from http://pexa.se/en/respiratory-research/.
"Pexa—The importance of early diagnosis", downloaded on Mar. 25, 2019 from http://pexa.se/en/respiratory-research/the-importance-of-early-diagnosis/.
"Pexa—The search for new biomarkers", downloaded on Mar. 25, 2019 from http://pexa.se/en/respiratory-research/the-search-for-new-biomarkers/.
Piao, Wen et al., "Development of azo-based fluorescent probes to detect different levels of hypoxia," Angew. Chem. Int. Ed. 2013, 52, 13028-13032.
Prodromidis, M.I., "Impedimetric immunosensors—A review", Electrochimica Acta, (May 30, 2010), 55(14):4227-33.
Quintela, Oscar et al., "Recovery of drugs of abuse from the immunalysis quantisal ™ oral fluid collection device," Journal of Analytical Toxicology, vol. 30, Oct. 2006.
Rahim S.A. et al., "Colorimetric determination of ethanol in the presence of methanol and other species in aqueous solution," Taianta. Nov. 1992;39(11):1489-91, PubMed abstract 18965558.
Restriction requirement dated Oct. 7, 2021, for U.S. Appl. No. 16/949,066.
Rohrich, J. et al., "Concentrations of delta9-tetrahydrocannabinol and 11-nor-9-carboxytetrahydrocannabinol in blood and urine after passive exposure to cannabis smoke in a coffee shop," Journal of Analytical Toxicology, vol. 34, May 2010.
Russo, E et al., "A tale of two cannabinoids: the therapeutic rational for combining tetrahydrocannabinol and cannabidiol," Med Hypotheses. 2006;66(2):234-46, PubMed abstract 16209908.
Saalberg, Yannick and Marcus Wolff, "VOC breath biomarkers in lung cancer", Clinica Chimica Acta, (Aug. 1, 2016), 459:5-9.
Samitas, K., et al., "Exhaled cysteinyl-leukotrienes and 8-isoprostane in patients with asthma and their relation to clinical severity", Respiratory medicine, (May 1, 2009), 103(5):750-6.
Samyn N. et al., "On-site testing of saliva and sweat with Drugwipe and determination of concentrations of drugs of abuse in saliva, plasma and urine of suspected users," Int J Legal Med. 2000;113(3):150-4, PubMed abstract 10876986.
Sarafian, Theodor et al., "Inhaled marijuana smoke disrupts mitochondrial energetics in pulmonary epithelial cells in vivo," Am J Physiol Lung Cell Mol Physiol, 2006, 290. L1202-L1209. (Year:2006).
Scheuplein, Robert J., "Mechanism of percutaneous absorption. II. Transient diffusion and the relative importance of various routes of skin penetration," J. Invest. Dermatol 1967;48:79.
Schwartz, Richard H. et al., "Laboratory detection of marijuana use, Experience with a photometric immunoassay to measure urinary cannabinoids," Aj J Dis Child. 1985;139(11): 1093-1096, abstract.
Schwilke, Eugene W. et al., "Delta9-tetrahydrocannabinol (THC), 11-hydroxy-THC, and 11-nor-9-carboxy-THC plasma pharmacokinetics during and after continuous high-dose oral THC," Clinical Chemistry 55:12 2180-2189 (2009).
Shaw, Leslie M. et al., "Ultrasensitive measurement of delta-9-tetrahydrocannabinol with a high energy dynode detector and electron-capture negative chemical-ionization mass spectrometry," Clin. Chem. 37/12, 2062-2068 (1991).
Sigma, "How Proximity Ligation Assays (PLA) Work".
Sivashanmugan K, Squire K, Tan A, Zhao Y, Kraai JA, Rorrer GL, Wang AX. Trace detection of tetrahydrocannabinol in body fluid via surface-enhanced Raman scattering and principal component analysis. ACS sensors. Mar. 25, 2019;4(4):1109-17.
Skopp, G. et al., "Partition coefficient, blood to plasma ratio, protein binding and short-term stability of 11-nor-Delta(9)-carboxy tetrahydrocannabinol glucuronide," Forensic Sci Int. Mar. 28, 2002;126(1):17-23, PubMed abstract 11955826.
Soares, J.R. et al., "Significant developments in radioimmune methods applied to delta9-THC and its 9-substituted metabolites," Analysis of Cannabinoids Research Monograph 42, NIDA 1982.
Stevenson H, Bacon A, Joseph KM, Gwandaru WR, Bhide A, Sankhala D, Dhamu VN, Prasad S. A rapid response electrochemical biosensor for detecting THC in saliva. Scientific reports. Sep. 3, 2019; 9(1):1-11. (11 pages) //9:12701 | https://doi.org/10.1038/s41598-019-49185-y.
Stiles PL, Dieringer JA, Shah NC, Van Duyne RP. Surface-enhanced Raman spectroscopy. Annu. Rev. Anal. Chem.. Jul. 19, 2008;1:601-26.

(56) References Cited

OTHER PUBLICATIONS

Stinchcomb, A.L. et al., "Human skin permeation of Delta8-tetrahydrocannabinol, cannabidiol and cannbinol," J Pharm Pharmacol. Mar. 2004;56(3):291-7, PubMed abstract 15025853.

Strano-Rossi, Sabina et al., "Analysis of stimulants in oral fluid and urine by gas chromatography-mass spectrometry II: Pseudophedrine," Journal of Analytical Toxicology, vol. 34, May 2010.

Switz, N. A., et al., "Low-Cost Mobile Phone Microscopy with a Reversed Mobile Phone Camera Lens", PloS one, (May 22, 2014), 9(5):e95330. 7 pages.

Tan, Chongxiao et al., "Direct detection of delta9-tetrahydrocannabinol in aqueous samples using a homogeneous increasing fluorescence immunoassay (HiFi)," Anal Bioaanal Chem, 2010. 8 pgs.

Teshima, N. et al., "Determination of acetone in breath", Analytica Chimica Acta, 2005, 535, pp. 189-199.

"The Chemistry of Phenols," Zvi Rappoport, editor, © 2003 John Wiley & Sons, Ltd. ISBN: 0-471-49737-1.

Toennes, Stefan W et al., "Pharmacokinetic properties of delta9-tetrahydrocannabinol in oral fluid of occasional and chronic users," Journal of Analytical Toxicology, vol. 34, May 2010.

Townsend, Doug, Ian Eustis, Mark Lewis, Steven Rodgers, Kevin Smith, Ariel Bohman, C. T. Shelton, and C. A. Sacramento. "The Determination of Total THC and CBD Content in Cannabis Flower by Fourier Transform Near Infrared Spectroscopy." (2018); Document No. 014329_01, 5 pages, accessed at perkinelmer.com/lab-solutions/resources/docs/app_determination_of_thc_and_cbd_cannabisflower.pdf.

Turner, Carton E et al., "Constituents of cannabis sativa I. XVII. A review of the natural constituents," J. Nat. Prod. 1980;43:169.

Ullman EF, Kirakossian H, Switchenko AC, Ishkanian J, Ericson M, Wartchow CA, Pirio M, Pease J, Irvin BR, Singh S, Singh R. Luminescent oxygen channeling assay (LOCI): sensitive, broadly applicable homogeneous immunoassay method. Clinical chemistry. Sep. 1, 1996;42(9):1518-26.

U.S. Appl. No. U.S. Appl. No. 15/981,797, inventors Michael Scott Lynn et al., filed May 16, 2018.

U.S. Appl. No. U.S. Appl. No. 16/124,181, inventors Michael Scott Lynn et al., filed Sep. 6, 2018.

U.S. Appl. No. U.S. Appl. No. 16/248,656, inventors Michael Scott Lynn et al., filed Jan. 15, 2019.

U.S. Appl. No. U.S. Appl. No. 16/563,839, inventors Michael Scott Lynn et al., filed Sep. 7, 2019.

U.S. Appl. No. U.S. Appl. No. 16/729,116, inventors Lynn et al., filed on Dec. 27, 2019 [HNDLP010CUS],.

U.S. Appl. No. U.S. Appl. No. 16/776,501, inventors Lynn et al., filed Jan. 29, 2020.

U.S. Appl. No. U.S. Appl. No. 16/949,065, inventors Gordon et al., filed Oct. 12, 2020.

U.S. Appl. No. U.S. Appl. No. 16/949,066, inventors Michael Scott Lynn et al., filed Oct. 12, 2020.

U.S. Appl. No. U.S. Appl. No. 17/247,926, inventors Michael Scott Lynn et al., filed Dec. 30, 2020.

U.S. Appl. No. U.S. Appl. No. 17/249,096, inventors Jeffrey Adam Stoll et al., filed Feb. 19, 2021.

U.S. Appl. No. U.S. Appl. No. 17/249,817, inventors Michael Scott Lynn et al., filed Mar. 15, 2021.

U.S. Appl. No. U.S. Appl. No. 17/301,507, inventors D'Ambrosio et al., filed Apr. 5, 2021.

U.S. Appl. No. U.S. Appl. No. 17/301,559, inventors Jeffrey Michael Scott Lynn et al., filed Apr. 7, 2021.

U.S. Appl. No. U.S. Appl. No. 17/301,974, inventors Friedman et al., filed Apr. 20, 2021.

U.S. Appl. No. U.S. Appl. No. 17/302,476, inventors Michael Scott Lynn et al., on May 4, 2021.

U.S. Appl. No. U.S. Appl. No. 17/302,801, inventors Stoll et al., filed May 12, 2021.

U.S. Non Final Office Action dated Dec. 17, 2021 in U.S. Appl. No. 16/790,457.

U.S. Non Final Office Action dated Jan. 6, 2022 in U.S. Appl. No. 16/425,943.

U.S. Appl. No. 14/641,412, Corrected Notice of Allowability dated Apr. 18, 2018.

U.S. Appl. No. 14/641,412, Final Office Action dated Dec. 5, 2016.

U.S. Appl. No. 14/641,412, Notice of Allowance dated Jan. 9, 2018.

U.S. Appl. No. 14/641,412, Office Action dated Jun. 26, 2017.

U.S. Appl. No. 14/641,412, Office Action dated May 19, 2016.

U.S. Appl. No. 14/997,405, Corrected Notice of Allowability dated Jun. 15, 2017.

U.S. Appl. No. 14/997,405, Notice of Allowance dated May 10, 2017.

U.S. Appl. No. 14/997,405, Office Action dated Jan. 9, 2017.

U.S. Appl. No. 15/143,328, Notice of Allowability dated May 18, 2017.

U.S. Appl. No. 15/143,328, Notice of Allowance dated Feb. 10, 2017.

U.S. Appl. No. 15/143,328, Notice of Allowance dated Jun. 14, 2017.

U.S. Appl. No. 15/143,328, Office Action dated Sep. 1, 2016.

U.S. Appl. No. 15/143,379, Notice of Allowability dated Jun. 13, 2017.

U.S. Appl. No. 15/143,379, Notice of Allowance dated Mar. 21, 2017.

U.S. Appl. No. 15/143,379, Office Action dated Oct. 25, 2016.

U.S. Appl. No. 15/217,151, Final Office Action dated Oct. 30, 2017.

U.S. Appl. No. 15/217,151, Notice of Allowance dated Dec. 22, 2017.

U.S. Appl. No. 15/217,151, Office Action dated Jan. 9, 2017.

U.S. Appl. No. 15/217,151, Office Action dated May 16, 2017.

U.S. Appl. No. 15/217,264, Final Office Action dated Aug. 16, 2017.

U.S. Appl. No. 15/217,264, Notice of Allowance dated Nov. 16, 2017.

U.S. Appl. No. 15/217,264, Office Action dated Mar. 20, 2017.

U.S. Appl. No. 15/217,264, Office Action dated Oct. 24, 2016.

U.S. Appl. No. 15/650,518, Notice of Allowance dated Feb. 1, 2018.

U.S. Appl. No. 15/650,518, Office Action dated Oct. 4, 2017.

U.S. Appl. No. 15/650,537, Notice of Allowance dated Apr. 24, 2019.

U.S. Appl. No. 15/650,537, Notice of Allowance dated Jun. 14, 2019.

U.S. Appl. No. 15/650,537, Office Action dated Mar. 29, 2019.

U.S. Appl. No. 15/875,195, Notice of Allowance dated Jan. 11, 2019.

U.S. Appl. No. 15/875,195, Office Action dated Apr. 19, 2018.

U.S. Appl. No. 15/943,123, Notice of Allowance dated Dec. 22, 2020.

U.S. Appl. No. 15/943,123, Notice of Allowance dated Nov. 12, 2020.

U.S. Appl. No. 15/943,123, Office Action dated Jun. 29, 2020.

U.S. Appl. No. 15/943,123, Office Action dated Mar. 6, 2020.

U.S. Appl. No. 15/958,616, Notice of Allowance dated Jan. 2, 2020.

U.S. Appl. No. 16/124,181, Notice of Allowance dated Jul. 12, 2021.

U.S. Appl. No. 16/124,181, Notice of Allowance dated Jul. 16, 2021.

U.S. Appl. No. 16/124,181, Notice to File Corrected Application Papers dated Jul. 21, 2021.

U.S. Appl. No. 16/425,943, Office Action dated Jan. 6, 2022

U.S. Appl. No. 16/676,562, Office Action mailed time frame.

U.S. Appl. No. 16/790,457, Office Action dated Dec. 17, 2021.

U.S. Appl. No. 16/823,113, Office Action mailed time frame.

U.S. Appl. No. 17/573,560, filed Jan. 11, 2022.

Vahimaa P et al., "Surface-Enhanced Raman Spectroscopy (SERS)," Institute of Photonics at the University of Eastern Finland, accessible at sway.com/s/XtgAoh8F5QewSEFL/embed.

Valiveti, S. et al., "In vitro/in vivo correlation studies fortransdermal delta 8-THC development," J Pharm Sci. May 2004;93(5):1154-64, PubMed abstract 15067692.

Van der Kooy, F. et al., "Cannabis smoke condensate I: The effect of different preparation methods on tetrahydrocannabinol levels," Inhalation Toxicology, 20:801-804, 2008.

Vinciguerra, V. et al., "Inhalation marijuana as an antiemetic for cancer chemotherapy," NY State J Med. Oct. 1988;88(10):525-7.

(56) References Cited

OTHER PUBLICATIONS

"Volatile Organic Compounds (VOC) as non-invasive biomarkers fora range of diseases", downloaded on Mar. 25, 2019 from https://www.owlstonemedical.com/science-technology/voc-biomarkers/.
Wall, M.E. et al., "Metabolism, disposition, and kinetics of delta-9-tetrahydrocannabinol in men and women," Clin Pharmacol Ther. Sep. 1983;34(3):352-63, PubMed abstract 6309462.
Wall, M.E. et al., "The metabolism of delta 9-tetrahydrocannabinol and related cannabinoids in man," J Clin Pharmacol. Aug.-Sep. 1981;21 (8-9 Suppl):178S-189S, PubMed abstract 6271823.
Walsh, J. Michael et al., "An evaluation of rapid point-of-collection oral fluid drug-testing devices," Journal of Analytical Toxicology, vol. 27, Oct. 2003.
Wan, G.H., et al., "Cysteinyl leukotriene levels correlate with 8-isoprostane levels in exhaled breath condensates of atopic and healthy children", Pediatric research (Nov. 2013), 74(5):584.
Wang, Ax, Kong X. Review of recent progress of plasmonic materials and nano-structures for surface-enhanced Raman scattering. Materials. Jun. 2015;8(6):3024-52.
Watanabe, K. et al., "Brain microsomal oxidation of delta 8- and delta 9- tetrahydrocannabinol," Biochem Biophys Res Commun. Nov. 30, 1988;157(1):75-80, PubMed abstract 2848522.
Widman, M. et al., "Metabolism of delta 1-tetrahydrocannabinol by the isolated perfused dog lung. Comparison with in vitro liver matabolism." J Phar Pharmacol. Nov. 1975;27(11):842-8, PubMed abstract 1493.
Wiegand, D.M. et al., "Evaluation of police officers' exposure to secondhand cannabis smoke at open-air stadium events", NIOSH health hazard evaluation report; HHE 2017-0174-335, (Mar. 2019), https://www.cdc.gov/niosh/hhe/reports/pdfs/2017-0174-3335.pdf.
Williams, P.L. et al., "Identification in human urine of delta 9-tetrahydrocannabinol-11-oic acid glucuronide: a tetrahydrocannabinol metabolite," J Pharm Pharmacol. Jul. 1980;32(7):445-8, PubMed abstract 6105177.
Wingert, William E., "Lowering cutoffs for initial and confirmation testing for cocaine and marijuana: large-scale study of effects on the rates of drug-positive results," Clinical Chemistry 43:1 100-103 (1997).
Written Opinion of the Searching Authority dated Apr. 6, 2020, for International Patent Application No. PCT/US2020/13553, 7 pages.
Written Opinion of the Searching Authority dated Jan. 23, 2020, for International Patent Application No. PCT/US2019/060342, 9 pages.
Yang HU, D'Archangel J, Sundheimer ML, Tucker E, Boreman GD, Raschke MB. Optical dielectric function of silver. Physical Review B. Jun. 22, 2015;91(23):235137.
Zajicek, J. et al., "Cannabinoids for treatment of spasticity and other symptoms related to multiple sclerosis (CAMS study): multicentre randomised placebo-controlled trial," Lancet. Nov. 8, 2003;362(9395):1517-26, abstract.
Zanconato, S., et al., "Leukotrienes and 8-isoprostane in exhaled breath condensate of children with stable and unstable asthma", Journal of Allergy and Clinical Immunology, (Feb. 1, 2004), 113(2):257-63.
Zhou, J., "Review of recent developments in determining volatile organic compounds in exhaled breath as biomarkers for lung cancer diagnosis", Analytica chimica acta, (Dec. 15, 2017), 996:1-9.
Zhu, H.J., Wang JS, Markowitz JS, Donovan JL, Gibson BB, Gefroh HA, DeVane CL., "Characterization of P-glycoprotein inhibition by major cannabinoids from marijuana", Journal of Pharmacology and Experimental Therapeutics. May 1, 2006;317(2):850-7.
Zias, Joe et al., "Early medical use of cannabis," Nature; May 20, 1993; 363,6426; Research Library Core p. 215.
Zuardi, A.W. et al., "Action of cannabidiol on the anxiety and other effects produced by delta 9-THC in normal subjects," Psychopharmacology (Berl). 1982;76(3):245-50, PubMed abstract 6285406.

\* cited by examiner

US 11,426,097 B1

ROTARY VALVE ASSEMBLIES AND METHODS OF USE FOR BREATH SAMPLE CARTRIDGE SYSTEMS

CROSS REFERENCE TO RELATED APPLICATIONS

This application claims the benefit and priority of U.S. Provisional Application Ser. No. 62/746,858 filed on Oct. 17, 2018 entitled "Breath Sample Cartridge and System". This application also claims the benefit and priority of U.S. Provisional Application Ser. No. 62/821,900 filed on Mar. 21, 2019 and entitled "Biomarker Detection from Breath Samples". Each of the above-referenced applications is hereby incorporated by reference herein in their entireties, including all references and appendices cited therein, for all purposes.

FIELD OF THE INVENTION

The present disclosure is directed generally to rotary valve assemblies that are configured for use in breath same cartridge systems. The rotary valve assemblies are adapted to translate from an open configuration to a closed configuration as desired.

SUMMARY

Some embodiments of the present disclosure can be directed to a device for breath capture and analysis. The device can comprise a cartridge housing comprising a breath capture module, and a rotary valve operatively coupling a mouthpiece with the breath capture module, the rotary valve having an open position where breath of a user can pass through the rotary valve, across capture sites of the breath capture module, and into a vacuum port, and a closed position for sealing the breath capture module from fluid passing through the rotary valve, while allowing the breath capture module to be exposed to a reagent for further analysis of one or more target chemicals that may be present in the breath. As used herein, the term fluid refers to the liquid phase or the gas phase.

Some embodiments of the present disclosure can be directed to a rotary valve that comprises a valve body operatively coupling a mouthpiece with a breath capture module, the valve body having a central aperture providing a path for the communication of breath across the breath capture module, and a sealing member is capable of sealing the breath capture module to prevent the breath from contacting the breath capture module. The valve body is configured to translate between an open position where the breath of a user passes through the central aperture of the valve body, across capture sites of the breath capture module, and into a vacuum port, and a closed position where the sealing member is sealing the breath capture module from fluid passing through the rotary valve, while allowing the breath capture module to be exposed to a reagent from a port associated with the breath capture module.

Some embodiments of the present disclosure can be directed to a rotary valve that comprises a valve body comprising a central aperture providing a path for the communication of breath across the breath capture module when the rotary valve is in an open position, and a sealing surface that is capable of created a seal against at least a portion of an upper surface of the breath capture module to prevent the breath from contacting the breath capture module when the rotary valve is in a closed position.

BRIEF DESCRIPTION OF THE DRAWINGS

The accompanying drawings, where like reference numerals refer to identical or functionally similar elements throughout the separate views, together with the detailed description below, are incorporated in and form part of the specification, and serve to further illustrate embodiments of concepts that include the claimed disclosure, and explain various principles and advantages of those embodiments.

The methods and systems disclosed herein have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

DETAILED DESCRIPTION

Generally speaking, the present disclosure is directed to rotary valves that are configured for use in breath sample cartridge systems. A rotary valve of the present disclosure can operatively couple a mouthpiece of a breath sample collection system to a breath capture module of the breath sample collection system. The rotary valve can translate between an open position and a closed position. When the rotary valve is in the open position the exhaled breath of a user can pass from the mouthpiece, through the rotary valve, and across the breath capture module. When the rotary valve is in the closed position, one or more sealing surfaces of the rotary valve abut inputs or outputs of the breath capture module, effectively preventing the breath of the user from passing over the breath capture module (or any other fluid such as ambient air). Further, when the rotary valve is in the closed position, the breath capture module can be exposed to a reagent for extraction and subsequent analyses of components within the collection breath. While the term "rotary valve" is used herein to describe exemplary embodiments, it will be understood by persons of ordinary skill in the art that other mechanisms that provide similar functionality may alternatively be utilized.

Figure 1:
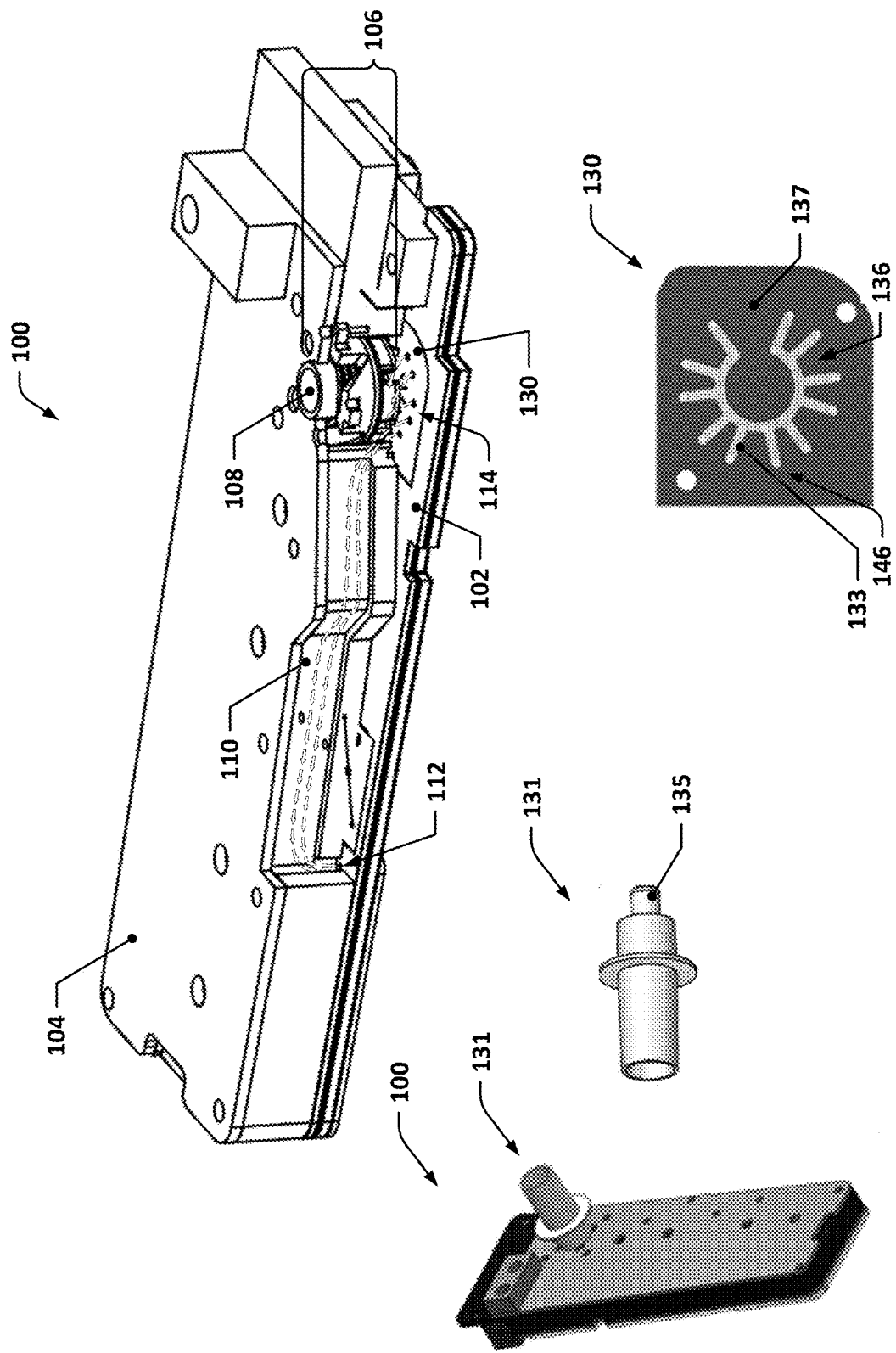
FIG. 1 illustrates an example breath sample cartridge system constructed in accordance with the present disclosure, specifically illustrating a breath capture module and rotary valve.

FIG. 1 depicts an example breath sample cartridge system 100 having a substrate 102 attached to a larger cartridge housing 104 that includes a rotary valve 106 having a breath sample receiving port 108, also referred to as a central aperture, which may, as discussed herein, be interfaced with a saliva trap and/or mouthpiece 131. The cartridge housing 104 may, as shown, have a vacuum passage 110 that is fluidically positioned between the exhaust passages 112 and a vacuum port 114 during breath sample collection.

The vacuum port 114 may, in turn, be fluidically coupled with a vacuum pump or pumps, e.g., within a handheld unit that may be connected with a cartridge during sample collection.

Figure 2:
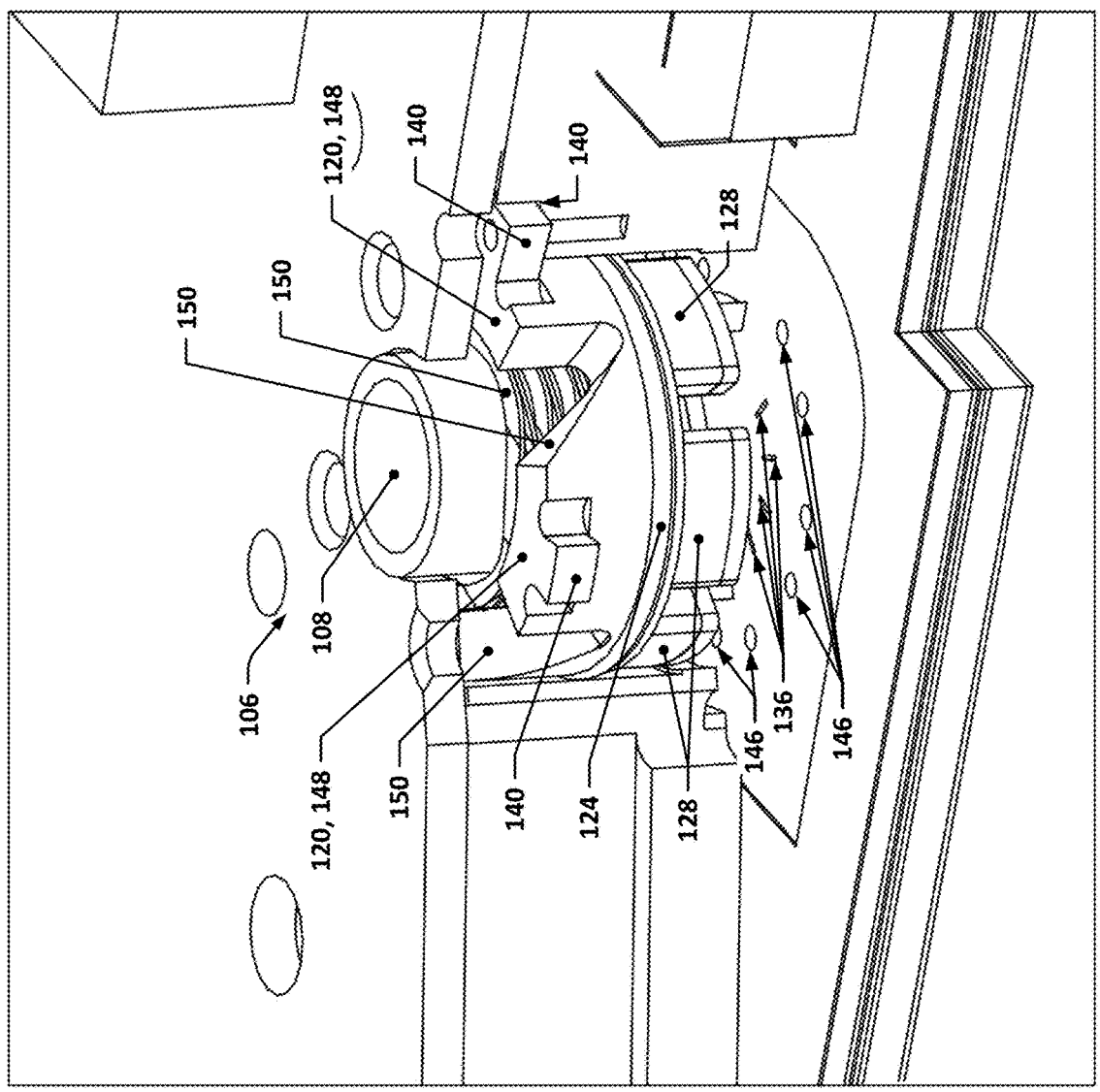
FIG. 2 is a perspective view of an example rotary valve of the present disclosure installed in an example breath sample cartridge system.
Figure 3:
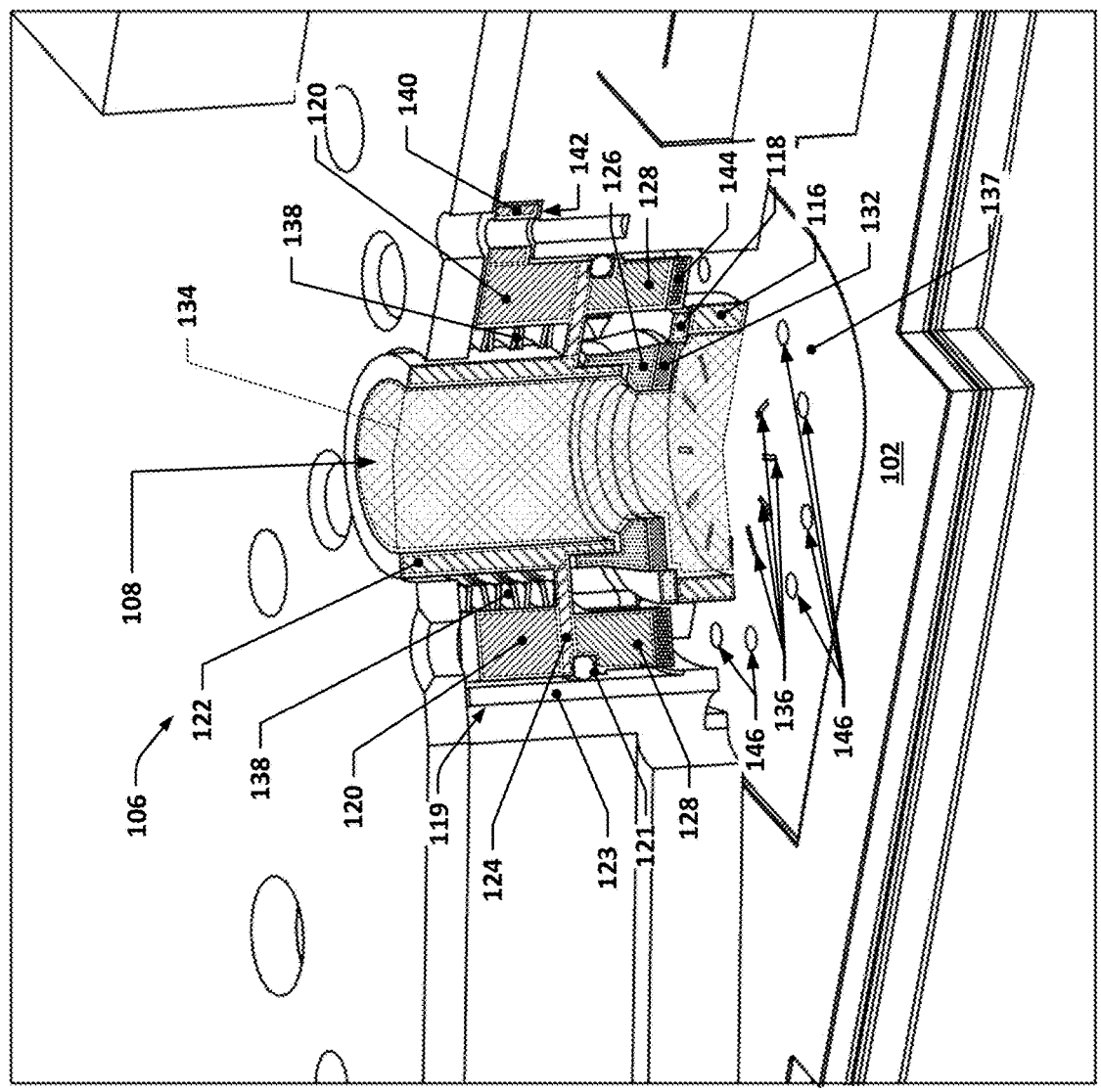
FIG. 3 is a perspective, cross-section view of the example rotary valve in an open configuration/position.
Figure 4:
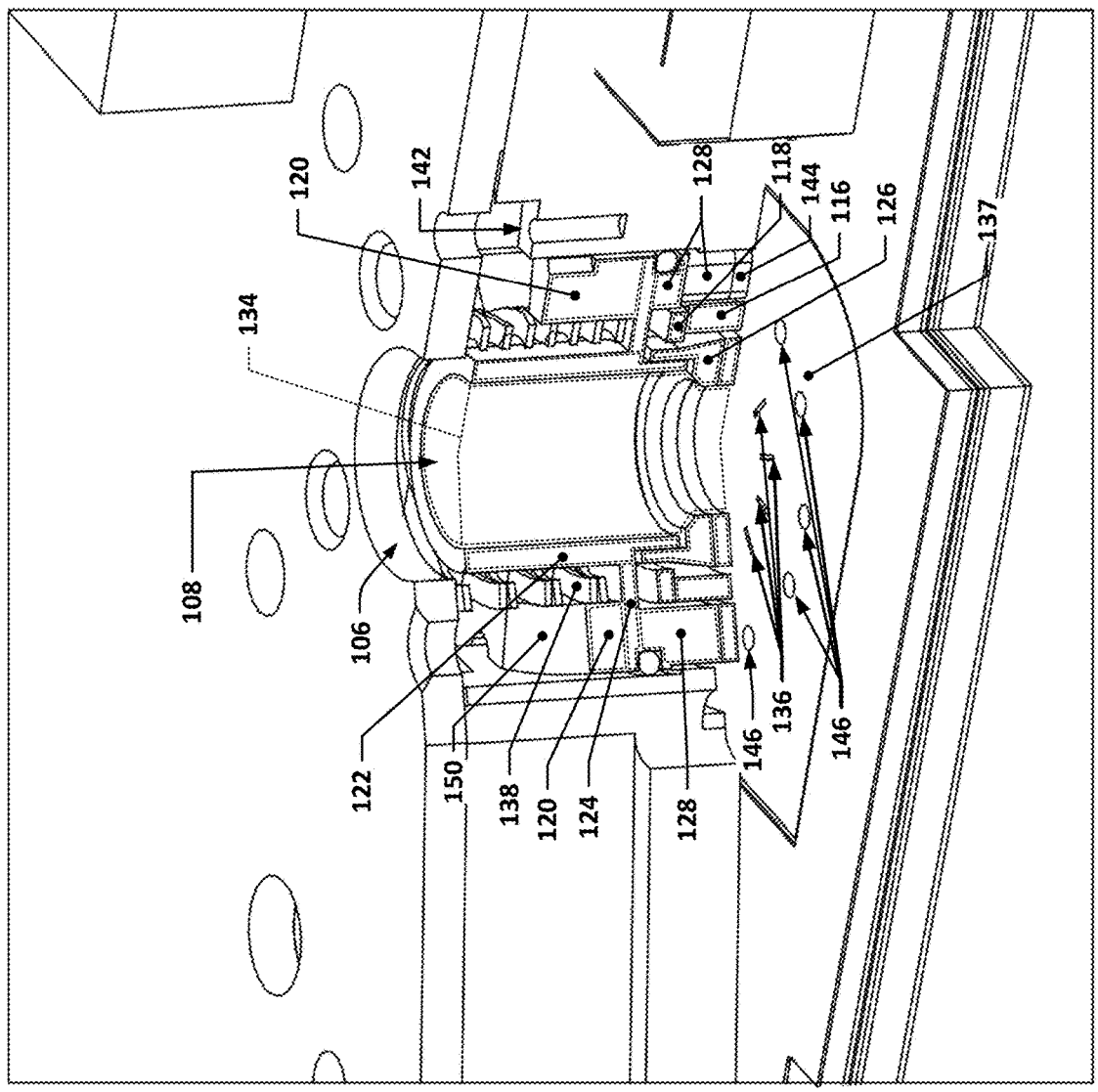
FIG. 4 is a perspective, cross-section view of the example rotary valve in a closed configuration/position.
Figure 5:
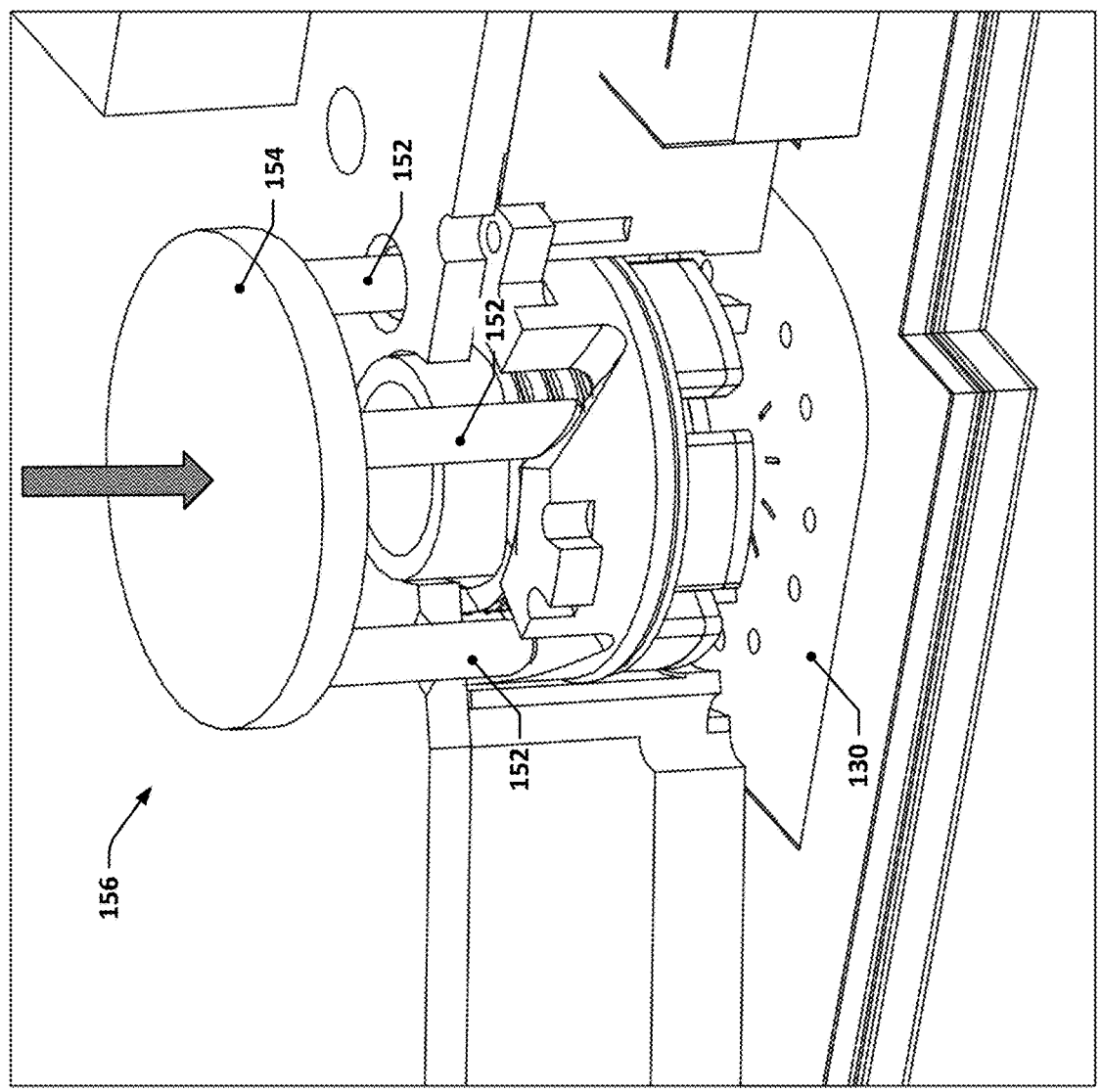
FIGS. 5 and 6 collectively illustrate the use of a tool to close the rotary valve.
Figure 6:
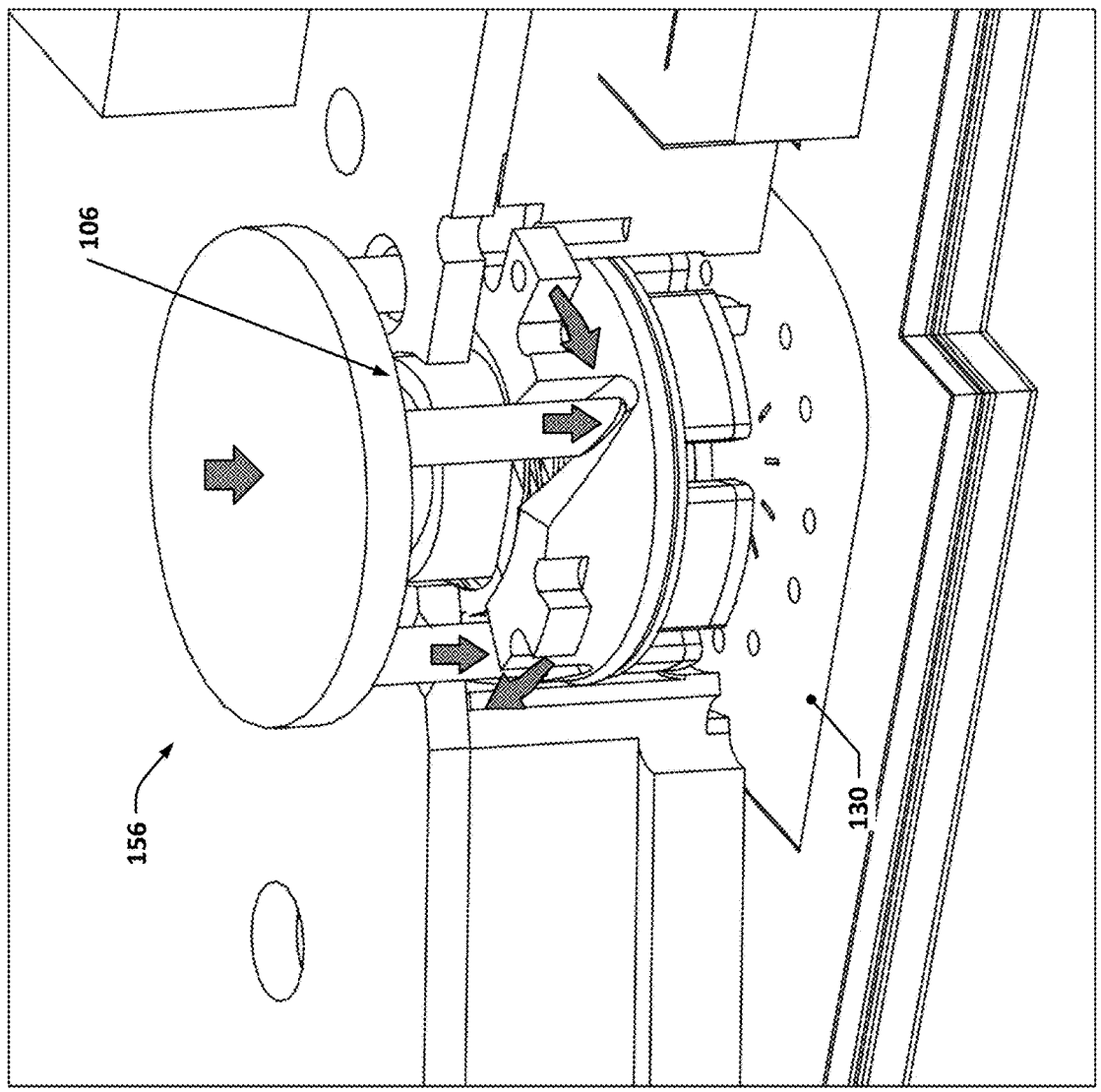
Figure 7:
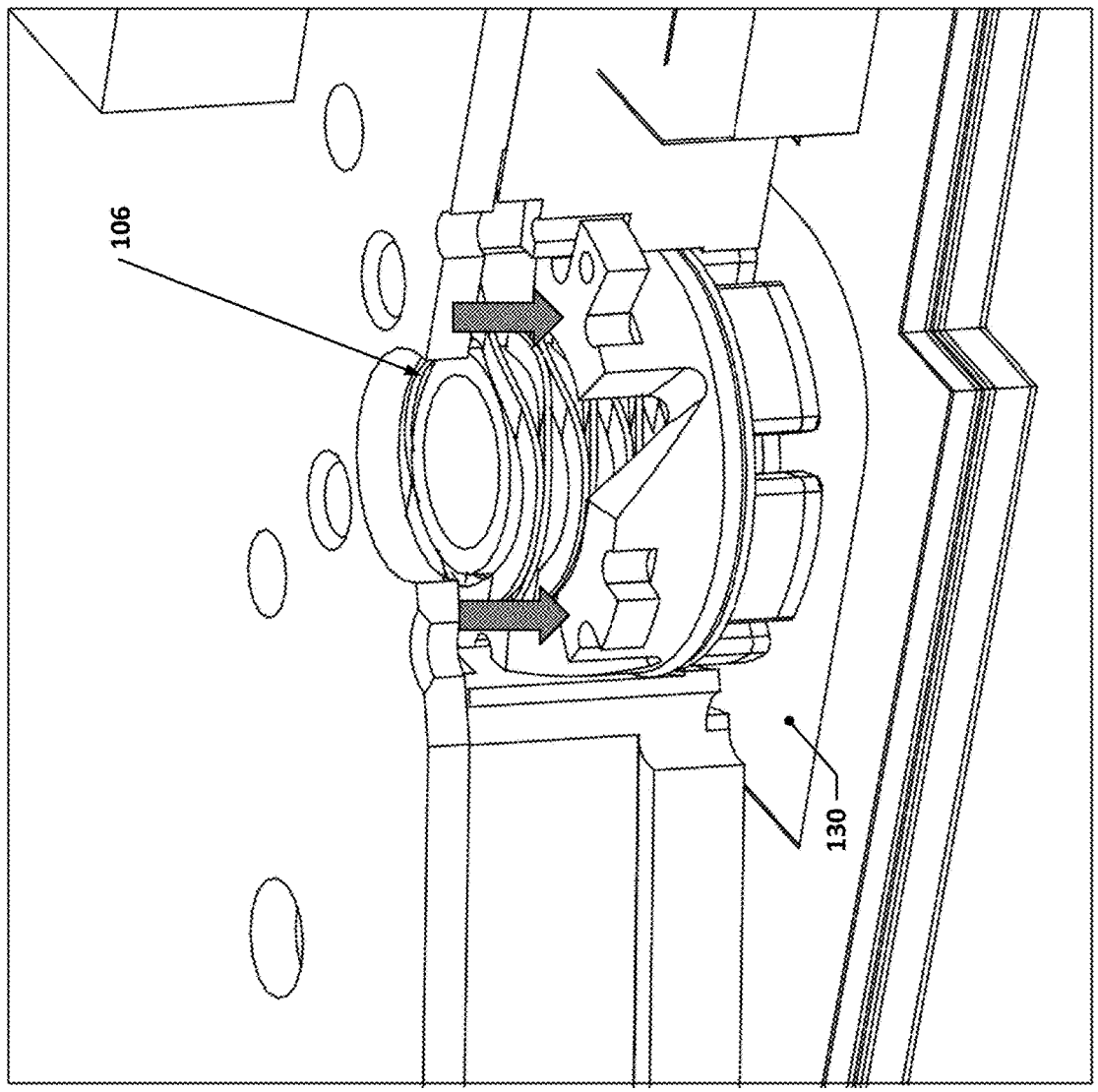
FIG. 7 illustrates the example rotary valve in a closed configuration/position after use of the tool.
Figure 8:
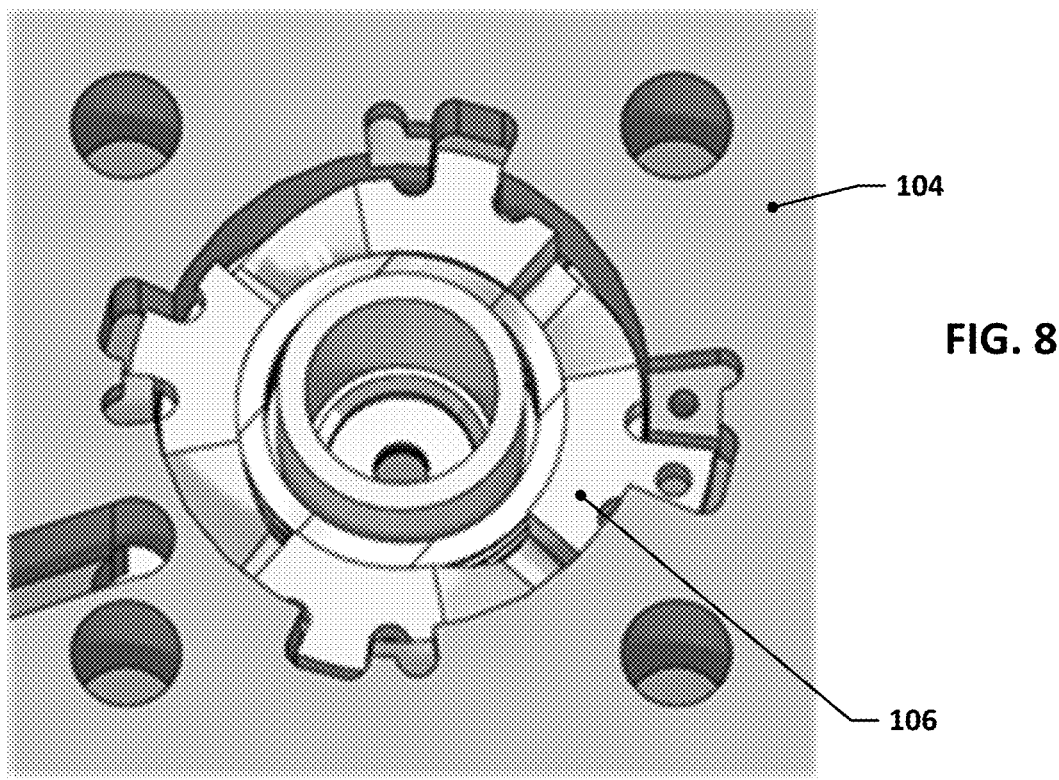
FIG. 8 depicts an exemplary view of an actuated rotary valve in a cartridge housing.
Figure 9:
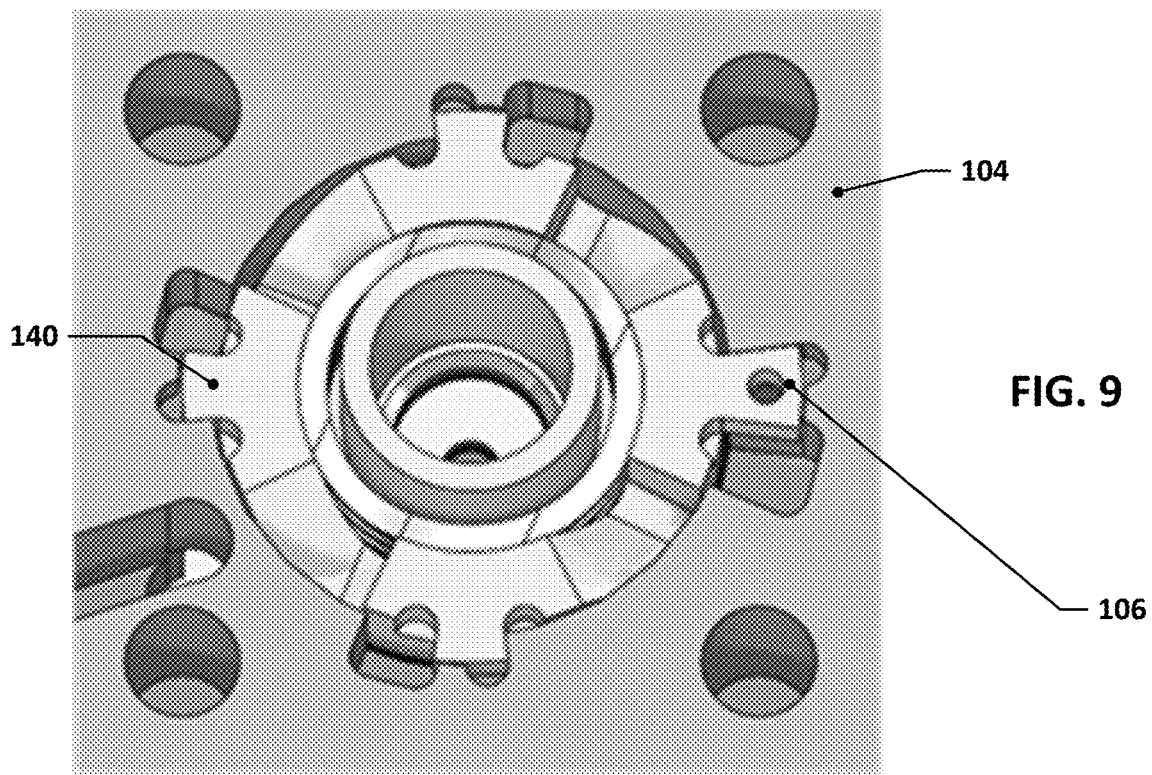
FIG. 9 depicts an exemplary view of a non-actuated rotary valve in a cartridge housing.
Figure 10:
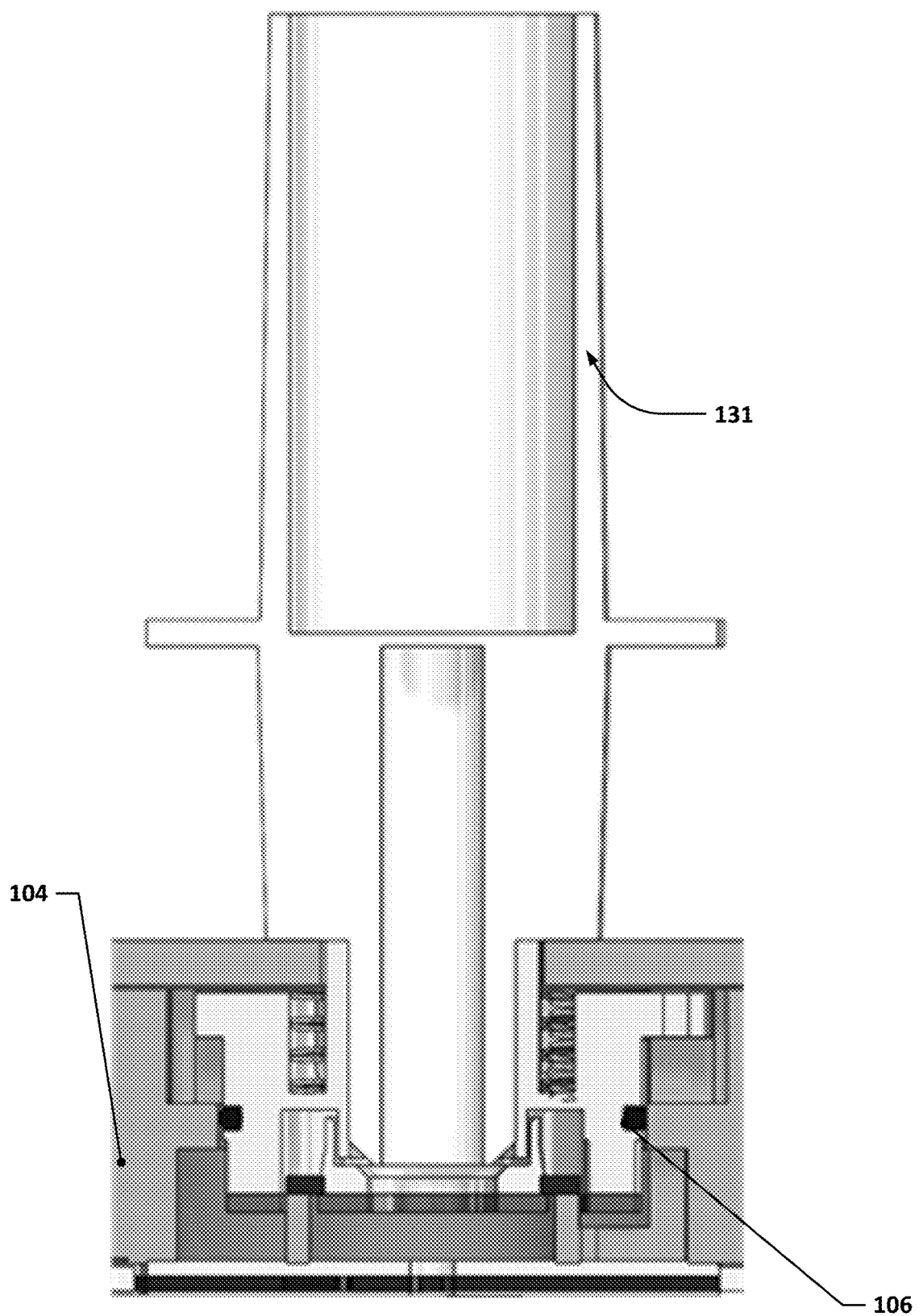
FIG. 10 depicts an exemplary cross-sectional side view of a rotary valve with a mouthpiece attached.
Figure 11:
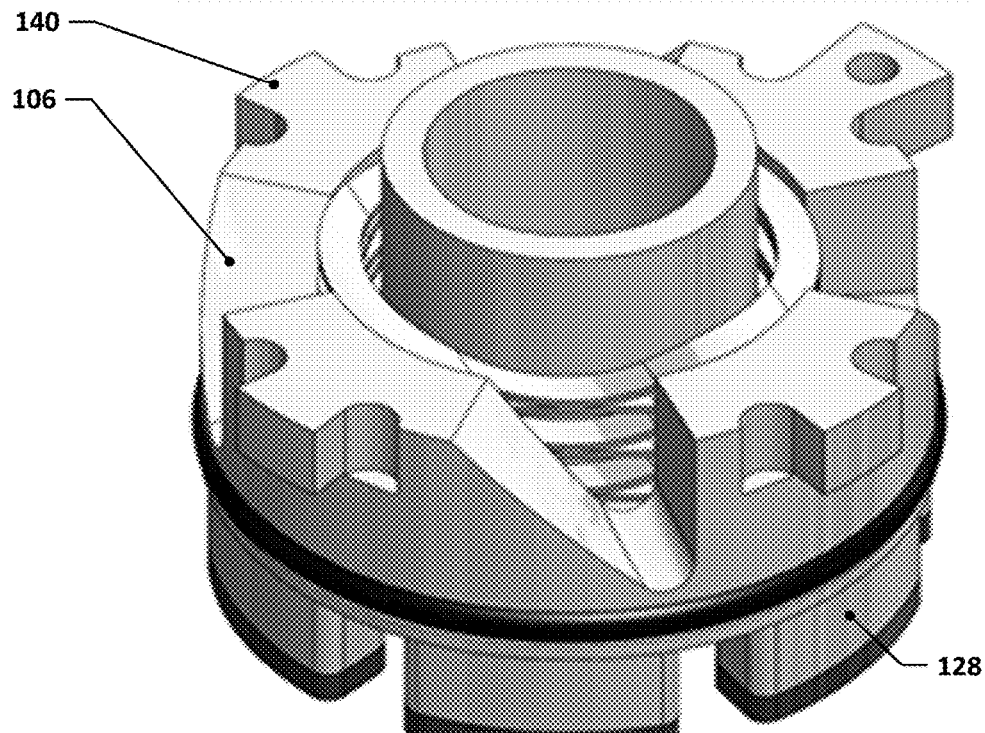
FIG. 11 depicts an exemplary isometric view of a rotary valve from the top and side.
Figure 12:
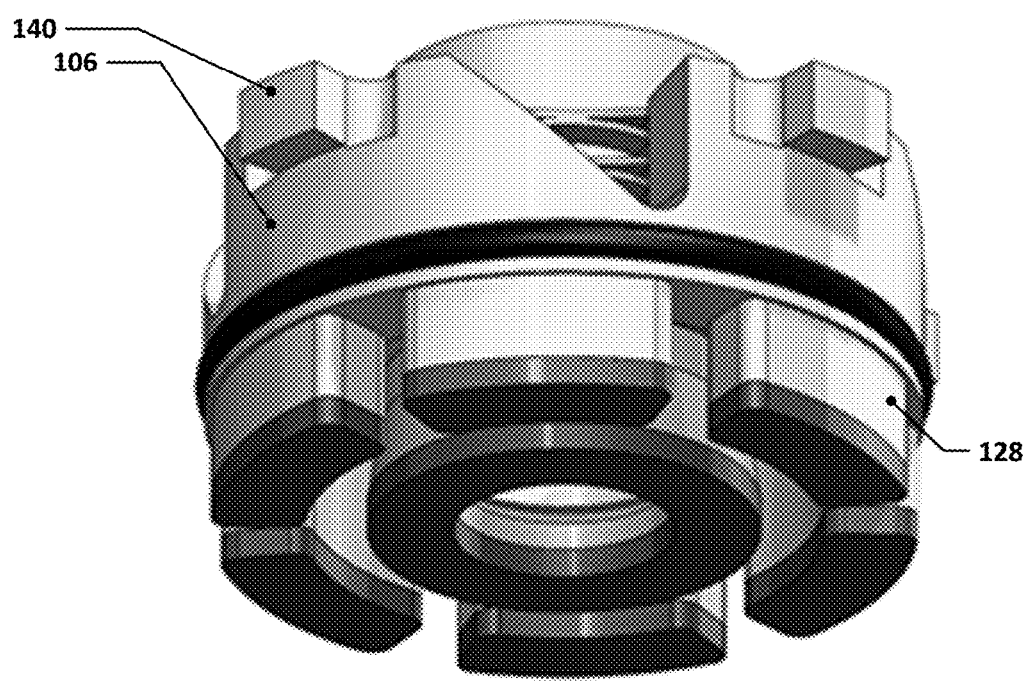
FIG. 12 depicts an exemplary isometric view of an underside of a rotary valve.
Figure 13:
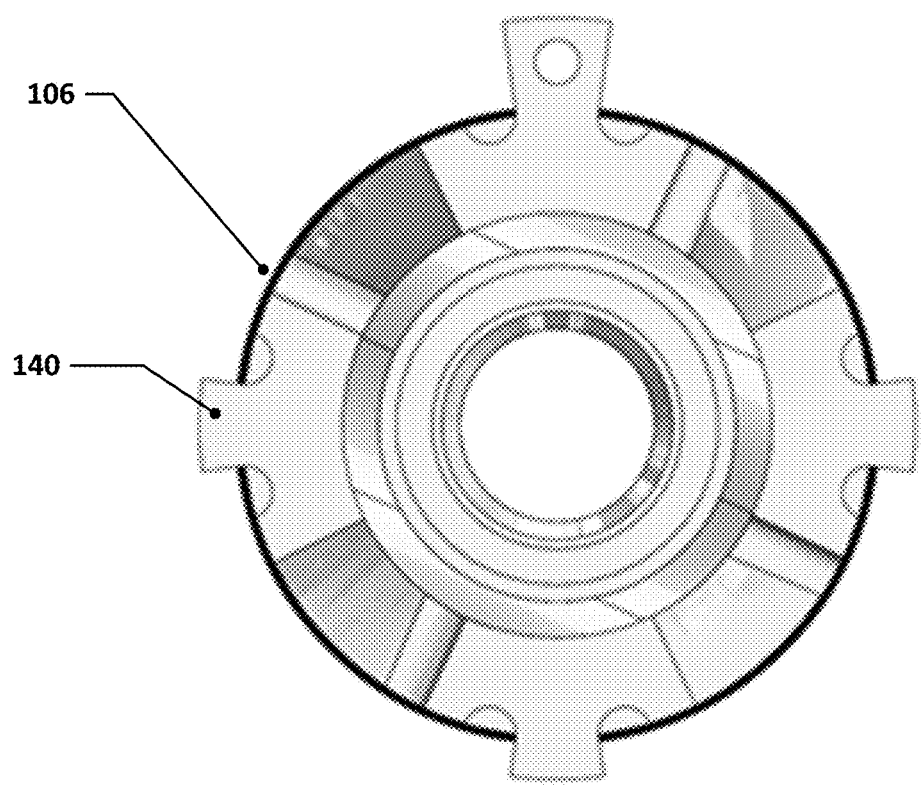
FIG. 13 depicts an exemplary top view of a rotary valve.
Figure 14:
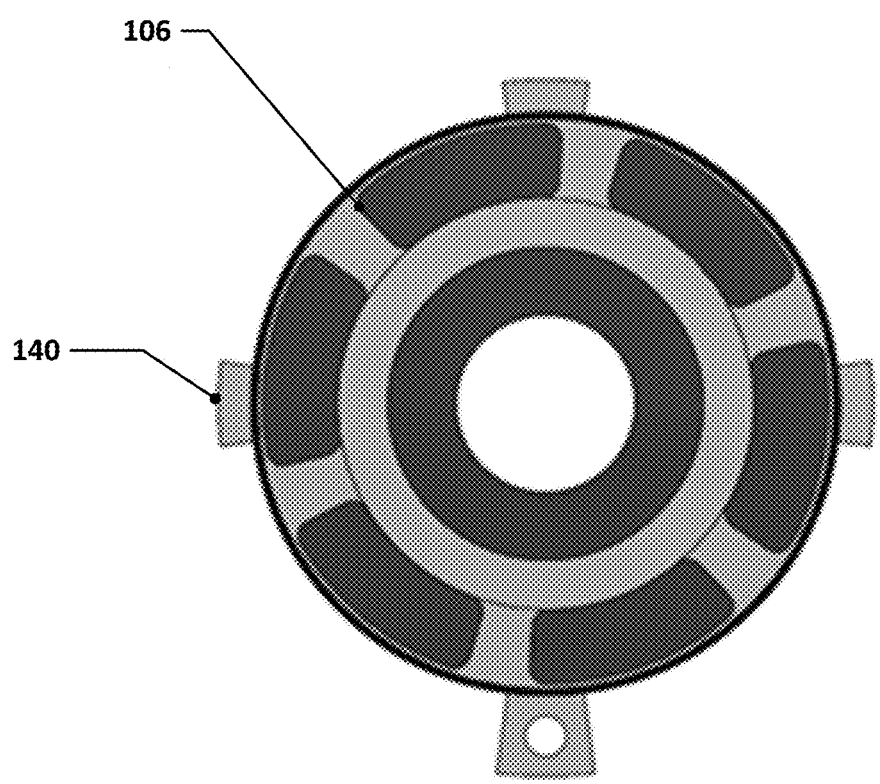
FIG. 14 depicts an exemplary underside view of a rotary valve.

FIG. 2 depicts a close-up of the rotary valve 106 of FIG. 1; FIGS. 3 and 4 show additional cutaway views of the rotary valve 106 in both an "open" configuration (FIG. 3) and a "closed" configuration (FIG. 4). The depicted valve structure is only one example of a valve structure that may be used with the droplet traps discussed herein; other valve structures may be used to provide similar functionality. In some implementations, no valve structure may be used at all, and the functionality provided by the valve structure may be provided by other means.

The following description will reference FIGS. 2-4 collectively. In the depicted rotary valve 106, the rotary valve 106 has a first portion that is fixed relative to the substrate 102. The first portion, in this example, includes the annular lower wall 116 and the annular lower wall seal 118. In general, the rotary valve 106 operatively couples a mouthpiece 131 with the breath capture module 130. In general, the first and second portions of the rotary valve are referred to as the valve body 119.

In some embodiments, a gasket, such as an o-ring 121 is disposed between the valve body 119 and a rotary valve receiver 123 of the cartridge housing 100. The o-ring 121 provides a seal between the valve body of the rotary valve and the rotary valve receiver in the cartridge housing.

The depicted rotary valve 106 may also include a second portion that is movable relative to the first portion and the substrate 102. The second portion, in this example, includes various features (shown in cross-section in FIGS. 3 and 4), such as, for example, an annular outer wall 120, a tubular inner structure 122, a circular base 124, a collar 126, and lower risers 128.

The tubular inner structure 122 defines a passageway into which a saliva trap, mouthpiece (see example mouthpiece 131), or other adapter may be inserted in order to allow a breath sample to be blown into a breath capture module 130. In general, the rotary valve 106 operatively couples a mouthpiece 131 with the breath capture module 130. That is, the rotary valve 106 provides a pathway for communication of the breath of a user to, and through, the breath capture module 130. In some embodiments, the mouthpiece 131 comprises a stem 135 that is configured to fit into the central aperture/breath sample receiving port 108 of the rotary valve 106.

In the open configuration/position, the breath of a user can pass through the rotary valve 106, across capture sites 133 of the breath capture module 130, and into a vacuum port 114 as a remainder of the breath (that portion which is not captured in the breath capture module 130) exits the breath capture module 130 from the exhaust ports 146.

The inner surfaces of the tubular inner structure 122, collar 126, and annular upper valve seal 132 of the second portion and the annular lower wall 116 and the annular lower wall seal 118 of the first portion may define a plenum volume 134 through which the breath sample may be flowed before flowing through the impaction ports 136 of the breath capture module 130. The plenum volume 134 may be generally sealed between the breath sample receiving port 108 and the impaction ports 136 when the valve structure is in the "open" configuration so as to allow a positive pressure to be developed within the plenum volume 134 during breath sampling.

In the depicted rotary valve 106, the second portion is able to translate along the center axis of the rotary valve 106, e.g., along a direction perpendicular to the substrate 102. A compression spring 138 may apply force to the second portion, e.g., by being compressed between the housing of the cartridge and the second portion, that urges the second portion towards the substrate 102 and into the "closed" configuration. In some embodiments, the compression spring 138 includes a plurality of stacked wave springs. In the closed configuration/position, the rotary valve seals the breath capture module 130 from fluid, such as breath, passing through the rotary valve 106, while allowing the breath capture module 130 to be exposed to a reagent. The exposure of the breath capture module 130 to reagents is beyond the scope of this disclosure.

The second portion may have a plurality of radial tabs 140 (also referred to as protrusions) that extend outwards from the annular outer wall 120 and that may rest on ledges 142 in the housing of the cartridge when the rotary valve 106 is in the "open" configuration. If the second portion is rotated about the center axis of the plenum 134 by a sufficient amount, e.g., 20°, this may cause the radial tabs 140 to no longer rest on the ledges 142, freeing the second portion to translate along that center axis towards the substrate 102 due to the force exerted by the compression spring 138. The lower risers 128 may be equipped with exhaust port seals 144, which may be made of a compliant material, as may be the case with the annular upper valve seal 132, in order to seal against the substrate 102 when in the closed configuration. In some embodiments, the exhaust port seals 144 seal the plurality of exhaust ports 146 of the breath capture module 130. The annular upper valve seal 132 seals against the impaction ports 136 of the breath capture module 130. To be sure, the exhaust port seals 144 and the annular upper valve seal press against elements of an upper surface 137 of the breath capture module 130. In various embodiments, the terminal ends of the exhaust port seals 144 comprise a closed-cell foam. The terminal end of the annular upper valve seal 132 can also comprise closed-cell foam. While closed-cell foam has been disclosed, other similar materials can likewise be utilized in accordance with the present disclosure. To be sure, other materials such as polymers, elastomers, hybrid materials (including foams and blends), as well as any other similar natural or composite materials ranging from flexible or rigid can also be used. To be sure, any material that would be known to one of ordinary skill in the art with the present disclosure before them can be selected that is capable of being used to create a seal against the exhaust ports 146 and the impaction ports 136.

Collectively, the exhaust port seals 144 and the annular upper valve seal 132 may be referred to generally in some embodiments as a sealing surface or member. In general, the sealing surface or member is capable of creating a seal against at least a portion of the upper surface 137 of the breath capture module 130.

In the depicted examples, the annular lower wall seal 118 is also made of a compliant material to allow the annular lower wall seal 118 and the annular upper valve seal 132 to seal against each other radially when in the closed configuration. In other configurations, the annular lower seal may simply seal radially against the rigid plastic of the annular lower wall 116. In yet other configurations, the annular upper valve seal 132 and the annular lower wall seal 118 may be provided by a single piece of material, which may be partially die cut such that the portion that corresponds with the annular upper valve seal 132 may tear free of the portion that corresponds with the annular lower wall seal 118 when the rotary valve 106 is transitioned to the closed configuration.

The depicted rotary valve 106 thus simultaneously seals the impaction ports 136 and the exhaust ports 146 of the exhaust passages (the second ends) when transitioned to the closed configuration; this seals the captured droplets (from the breath sample) inside of the breath capture module 130, allowing for the collected sample in the captured droplets to be eluted or otherwise fluidically manipulated without leaking back out of the impaction ports 136 or through the exhaust passages 112. FIGS. 5 through 7 collectively depict the closure of the valve structure in the depicted examples.

Referring back to FIG. 2, it will be noted that the annular outer wall 120 includes a series of crenellations 148 that each have a sloped side 150. Additionally, the housing may have a hole located above each such sloped surface, allowing posts 152 (referring back to FIG. 5) attached to a load distributor 154 of actuator key 156 to be inserted therethrough and engage with the sloped sides 150. When compressive force is applied to the load distributor 154, the posts 152 are urged downward onto the sloped sides 150, causing the second portion to rotate so that the posts "slide" down the sloped sides 150—in this example, such rotation is clockwise (when looking along the compression direction) and causes the radial tabs 140 to rotate clear of the ledges 142 so that the latching mechanism provided by the radial tabs and ledges releases and allows the second portion to move relative to the first portion and enter the "closed" configuration, as shown in FIGS. 6 and 7.

The rotary valve and breath capture components discussed herein can be utilized in a breath sample capture and analysis system. In exemplary embodiments, when the rotary valve is in the closed position, the captured breath sample in the breath collection module can be subject to additional analysis on a cartridge. Elution or other means for capturing target components in the collected breath can be utilized for collecting a sample on a cartridge for further analysis. Additionally, means for concentrating a target component can also be utilized. In exemplary embodiments, the cartridge can be a single-use microfluidic cartridge.

FIG. 8 depicts an exemplary view of an actuated rotary valve 106 in a cartridge housing 104. FIG. 9 depicts an exemplary view a non-actuated rotary valve 106 in a cartridge housing 104. As shown in the two figures, the radial tabs 140 of rotary valve 140 translate when moving from a non-actuated (open) position to an actuated (closed) position.

FIG. 10 depicts an exemplary cross-sectional side view of a rotary valve 106 in a cartridge housing 104, with attached mouthpiece 131. As discussed herein, a user blows into mouthpiece 131 until a target amount of breath is captured by the device. Then the rotary valve 106 is engaged to seal off mouthpiece 131 such that no further air can enter through it into the breath capture module and components of the cartridge. It will be understood by persons of ordinary skill in the art that the components in the exemplary figure are not necessary depicted according to scale. That is, the size of the components can be altered with respect to one another and still be within the scope of this disclosure.

FIG. 11 depicts an exemplary isometric view of rotary valve 106. FIG. 12 depicts an exemplary isometric view of an underside of rotary valve 106. In each view, rotary valve 106 has at least lower risers 128 and radial tabs 140 extending outward from the annular outer wall of rotary valve 106.

FIG. 13 depicts an exemplary top view of rotary valve 106, and FIG. 14 depicts an exemplary underside view of rotary valve 106. The rotary valve 106 depicted in these exemplary views is the same as rotary valve 106 depicted in FIG. 11 and FIG. 12.

The corresponding structures, materials, acts, and equivalents of all means or step plus function elements in the claims below are intended to include any structure, material, or act for performing the function in combination with other claimed elements as specifically claimed. The description of the present technology has been presented for purposes of illustration and description, but is not intended to be exhaustive or limited to the present technology in the form disclosed. Many modifications and variations will be apparent to those of ordinary skill in the art without departing from the scope and spirit of the present technology. Exemplary embodiments were chosen and described in order to best explain the principles of the present technology and its practical application, and to enable others of ordinary skill in the art to understand the present technology for various embodiments with various modifications as are suited to the particular use contemplated.

If any disclosures are incorporated herein by reference and such incorporated disclosures conflict in part and/or in whole with the present disclosure, then to the extent of conflict, and/or broader disclosure, and/or broader definition of terms, the present disclosure controls. If such incorporated disclosures conflict in part and/or in whole with one another, then to the extent of conflict, the later-dated disclosure controls.

The terminology used herein can imply direct or indirect, full or partial, temporary or permanent, immediate or delayed, synchronous or asynchronous, action or inaction. For example, when an element is referred to as being "on," "connected" or "coupled" to another element, then the element can be directly on, connected or coupled to the other element and/or intervening elements may be present, including indirect and/or direct variants. In contrast, when an element is referred to as being "directly connected" or "directly coupled" to another element, there are no intervening elements present.

Although the terms first, second, etc. may be used herein to describe various elements, components, regions, layers and/or sections, these elements, components, regions, layers and/or sections should not necessarily be limited by such terms. These terms are only used to distinguish one element, component, region, layer or section from another element, component, region, layer or section. Thus, a first element, component, region, layer or section discussed below could be termed a second element, component, region, layer or section without departing from the teachings of the present disclosure.

The terminology used herein is for the purpose of describing particular embodiments only and is not intended to be necessarily limiting of the disclosure. As used herein, the singular forms "a," "an" and "the" are intended to include the plural forms as well, unless the context clearly indicates otherwise. The terms "comprises," "includes" and/or "comprising," "including" when used in this specification, specify the presence of stated features, integers, steps, operations, elements, and/or components, but do not preclude the presence or addition of one or more other features, integers, steps, operations, elements, components, and/or groups thereof.

Example embodiments of the present disclosure are described herein with reference to illustrations of idealized embodiments (and intermediate structures) of the present disclosure. As such, variations from the shapes of the illustrations as a result, for example, of manufacturing techniques and/or tolerances, are to be expected. Thus, the example embodiments of the present disclosure should not be construed as necessarily limited to the particular shapes of regions illustrated herein, but are to include deviations in shapes that result, for example, from manufacturing.

Any and/or all elements, as disclosed herein, can be formed from a same, structurally continuous piece, such as being unitary, and/or be separately manufactured and/or connected, such as being an assembly and/or modules. Any and/or all elements, as disclosed herein, can be manufactured via any manufacturing processes, whether additive manufacturing, subtractive manufacturing and/or other any other types of manufacturing. For example, some manufacturing processes include three dimensional (3D) printing, laser cutting, computer numerical control (CNC) routing, milling, pressing, stamping, vacuum forming, hydroforming, injection molding, lithography and/or others.

Any and/or all elements, as disclosed herein, can include, whether partially and/or fully, a solid, including a metal, a mineral, a ceramic, an amorphous solid, such as glass, a glass ceramic, an organic solid, such as wood and/or a polymer, such as rubber, a composite material, a semiconductor, a nano-material, a biomaterial and/or any combinations thereof. Any and/or all elements, as disclosed herein, can include, whether partially and/or fully, a coating, including an informational coating, such as ink, an adhesive coating, a melt-adhesive coating, such as vacuum seal and/or heat seal, a release coating, such as tape liner, a low surface energy coating, an optical coating, such as for tint, color, hue, saturation, tone, shade, transparency, translucency, non-transparency, luminescence, anti-reflection and/or holographic, a photo-sensitive coating, an electronic and/or thermal property coating, such as for passivity, insulation, resistance or conduction, a magnetic coating, a water-resistant and/or waterproof coating, a scent coating and/or any combinations thereof.

Unless otherwise defined, all terms (including technical and scientific terms) used herein have the same meaning as commonly understood by one of ordinary skill in the art to which this disclosure belongs. The terms, such as those defined in commonly used dictionaries, should be interpreted as having a meaning that is consistent with their meaning in the context of the relevant art and should not be interpreted in an idealized and/or overly formal sense unless expressly so defined herein.

Furthermore, relative terms such as "below," "lower," "above," and "upper" may be used herein to describe one element's relationship to another element as illustrated in the accompanying drawings. Such relative terms are intended to encompass different orientations of illustrated technologies in addition to the orientation depicted in the accompanying drawings. For example, if a device in the accompanying drawings is turned over, then the elements described as being on the "lower" side of other elements would then be oriented on "upper" sides of the other elements. Similarly, if the device in one of the figures is turned over, elements described as "below" or "beneath" other elements would then be oriented "above" the other elements. Therefore, the example terms "below" and "lower" can, therefore, encompass both an orientation of above and below.

In this description, for purposes of explanation and not limitation, specific details are set forth, such as particular embodiments, procedures, techniques, etc. in order to provide a thorough understanding of the present invention. However, it will be apparent to one skilled in the art that the present invention may be practiced in other embodiments that depart from these specific details.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" or "according to one embodiment" (or other phrases having similar import) at various places throughout this specification are not necessarily all referring to the same embodiment. Furthermore, the particular features, structures, or characteristics may be combined in any suitable manner in one or more embodiments. Furthermore, depending on the context of discussion herein, a singular term may include its plural forms and a plural term may include its singular form.

What is claimed is:

1. A device, comprising:
    a cartridge housing comprising a breath capture module; and
    a rotary valve operatively coupling a mouthpiece with the breath capture module, the rotary valve having:
        an open position where breath of a user can pass through the rotary valve, across capture sites of the breath capture module, and into a vacuum port; and
        a closed position for sealing the breath capture module from fluid passing through the rotary valve, while allowing the breath capture module to be exposed to a reagent, wherein rotation of the rotary valve from the open position to the closed position causes protrusions of a valve body to rotate, allowing exhaust port seals and an annular upper valve seal to move downwardly to cover inputs and outputs of the breath capture module.

2. The device according to claim 1, wherein a central aperture of the rotary valve is configured to receive a stem of the mouthpiece.

3. The device according to claim 1, wherein the valve body having has a central aperture.

4. The device according to claim 3, wherein the valve body is coupled to the cartridge housing via a spring.

5. The device according to claim 4, wherein the protrusions are configured to rest on ledges of the cartridge housing when the rotary valve is in the open position.

6. The device according to claim 5, wherein the protrusions do not rest on the ledges when the rotary valve is in the closed position.

7. The device according to claim 6, wherein the exhaust port seals and the annular upper valve seal comprise gaskets that seal the inputs and outputs of the breath capture module.

8. The device according to claim 1, further comprising a gasket that provides a seal between the valve body of the rotary valve and a rotary valve receiver in the cartridge housing.

9. A rotary valve, comprising:
    a valve body operatively coupling a mouthpiece with a breath capture module, the valve body having a central aperture providing a path for communication of breath across the breath capture module, wherein the valve body is configured to translate between:
   an open position where the breath of a user passes through the central aperture of the valve body, across capture sites of the breath capture module, and into a vacuum port; and
   a closed position where the valve body seals the breath capture module from fluid passing through the rotary valve while allowing the breath capture module to be exposed to a reagent from a port associated with the breath capture module.

10. The rotary valve according to claim 9, further comprising one or more wave springs that exert a force on the valve body along an axis that the valve body translates along when translating between the open position and the closed position, when the valve body is translated from the open position to the closed position to secure the valve body against the breath capture module.

11. The rotary valve according to claim 9, wherein the valve body comprises exhaust port seals and an annular upper valve seal that engage with inputs and outputs of the breath capture module when in the closed position.

12. The rotary valve according to claim 11, wherein each of the exhaust port seals and the annular upper valve seal includes a closed-cell foam gasket.

13. A rotary valve, comprising:
   a valve body comprising:
      a central aperture providing a path for communication of breath into a breath capture module when the rotary valve is in an open position; and
      a sealing surface that is configured to create a seal against at least a portion of an upper surface of the breath capture module to prevent the breath from flowing into the breath capture module when the rotary valve is in a closed position, wherein the sealing surface comprises exhaust port seals and an annular upper valve seal.

14. The rotary valve according to claim 13, wherein when the rotary valve is in the open position the breath of a user passes across capture sites of the breath capture module, and into a vacuum port.

15. The rotary valve according to claim 13, wherein a reagent is flowable through the breath capture module without the reagent exiting the breath capture module via inputs or outputs of the breath capture module when the rotary valve is in the closed position.

16. The rotary valve according to claim 13, wherein the annular upper valve seal comprises a closed-cell foam that engages with inputs or outputs of the breath capture module.

17. The rotary valve according to claim 13, wherein the sealing surface prevents the breath from moving across capture sites of the breath capture module.

18. The rotary valve according to claim 13, wherein the valve body is coupled to a cartridge housing via a spring, the valve body being configured to translate along an axis about which the valve body is configured to rotate within the cartridge housing.

19. The rotary valve according to claim 13, wherein the central aperture of the valve body is configured to receive a stem of a mouthpiece.

* * * * *